United States Patent [19]

Kroll

[11] Patent Number: 5,591,209
[45] Date of Patent: Jan. 7, 1997

[54] IMPLANTABLE DEFIBRILLATOR SYSTEM FOR GENERATING AN ACTIVE BIPHASIC WAVEFORM

[75] Inventor: Mark W. Kroll, Minnetonka, Minn.

[73] Assignee: Angeion Corporation, Plymouth, Minn.

[21] Appl. No.: 246,007

[22] Filed: May 19, 1994

[51] Int. Cl.$^6$ ...................................................... A61N 1/39
[52] U.S. Cl. .................................................. 607/5; 607/74
[58] Field of Search ........................................ 607/5, 7, 74

[56] References Cited

U.S. PATENT DOCUMENTS

| | | | |
|---|---|---|---|
| 3,527,229 | 9/1970 | Kempen | 607/5 |
| 3,566,876 | 3/1971 | Stoft et al. | 607/5 |
| 4,850,357 | 7/1989 | Bach . | |
| 4,998,531 | 3/1991 | Bocchi et al. . | |
| 5,083,562 | 1/1992 | de Coriolis et al. . | |

OTHER PUBLICATIONS

Kroll, M W et al., Pace 1993; 16 #1:213–217.
Bardy, GH et al., J. American College of Cardiology, 1989; 14:728–733.
Wyse, DG et al., American J. Cardiology 1993; 71:197–202.
Schuder, JC et al., Circulation Research, 1964; 15:258–264.
Kavanagh, KM et al., J. American College of Cardiology, 1989; 14:1343–1349.
Feeser, SA et al., Circulation, 1990; 82:2128–2141.
Walker, RG et al., Circulation 1992; 86 No. 4:I–792 (Abstract).
Gurvich, NL et al., Kardiologilia 1967; 7:109–112.
Tchou, P et al., Pace 1990; 13:506 (Abstract).
Jones JL, et al., American J. Physiology 1987; 253:H 1418–H 1424.
Kavanagh KM et al., Pace 1990: 13, 1268–1276.
Swartz JF, et al., Circulation Research 1991; 68–438–449.
Karasik P, et al., Pace 1991; 14:715 (Abstract).
Tang ASL et al., J. American College of Cardiology 1989; 13:207–14.
Bourland JD et al., Medical Instrumentation 1978; 12 #1:38–41.
Kroll MW, Adams TP, American Heart Journal 1992; 124 #3:835 (Abstract).
Irnich W, Pace 1980; 8:870–888.
Swartz JF, et al., Pace 1993; 16 #4II:888 (Abstract).
Ideker RE, et al., Cardiac Pacing and Electrophysiology 3rd Ed., edited by El–Sherif N & Samatt, WB Saunders Co. Philadelphia 1991; 42:713–726.
Frazier DW, et al., J. of Clinical Investigation 1989; 83:1039.
Shibata N, et al., American J. Physiology 1988; 255: H 902–H 909.
Zhou X, et al., Circulation Research 1993; 72:145–160.
Jones JL, Jones RE, American J. Physiology 1984; 247: H 792–H 796.
Niebauer MJ, et al., Medical and Biological Engineering and Computing 1984; 22:28–31.
Chapman PD, et al., J. American College of Cardiology 1988 12:739–745.
Dixon EF, Circulation 1987; 76:1176–1184.
Chapman, et al., J. American College of Cardiology 1988; 12:739–745.

(List continued on next page.)

*Primary Examiner*—William E. Kamm
*Assistant Examiner*—Kennedy J. Schaetzle
*Attorney, Agent, or Firm*—Patterson & Keough, P.A.

[57] ABSTRACT

An implantable cardioverter defibrillator for generating biphasic waveforms to treat cardiac dysrhythmias creates the second phase of the biphasic waveform from an active low energy source, rather than from a capacitive charge storage system. A high voltage first phase of the biphasic waveform is generated from the charge stored in a typical capacitive charge storage system. A low voltage second phase is generated from the continuous discharge of an active low voltage power source. By using an active low voltage power source system to directly produce the second phase of the biphasic waveform, the overall size and power requirements of the implantable device can be reduced.

17 Claims, 10 Drawing Sheets

OTHER PUBLICATIONS

Dillon SM, Circulation 1992; 85: 1865–1878.
Sweeney RJ, et al., Circulation 1990; 82 965–972.
Belz MK, et al., Pace 993; 16:932 (Abstract).
Frazier DW, et al., Circulation 1988; 63: 147–164.
Wessale JL et al., J. Electrocardiology 1980; 13(4):359–366.
Niebauer MJ, et al., Crit. Care Medicine 1983; 11 #2:95–98.
Wharton JM, et al., Pace 1990; 13:1158–1172.
Daubert JP, et al., Circulation 1991; 84:2522–2538.
Zhou X, et al., Circulation Research 1991; 68:1761–1767.
Yabe S, et al., Circulation Research 1990; 66:1190–1203.
Fozzard HA, J. Physiol (Great Britian) 1966; 182:255–267.
Weidmann S, J Physiol (Great Britian) 1970; 210:1041–1054.

Knisley SB, Circulation Research 1993; 72:255–270.

Jan. CT, Shorofsky S., J. Cardiovascular Electrophysiology 1990; 1:161–169.

Chen PS, et al., J. Clinical Investigation 1986; 77:810–823.

Hodgkin AL, Proc. Roayl Society, 1938; 126:87–121.

Cooley JW, Dodge FA., Biophysical Journal 1966; 6:583–599.

Krassowska W, et al., Pace 1992; 15:197–210.

Kao CY, Hoffman BF, American J. Physiology 1958; 194(1):187P14 196.

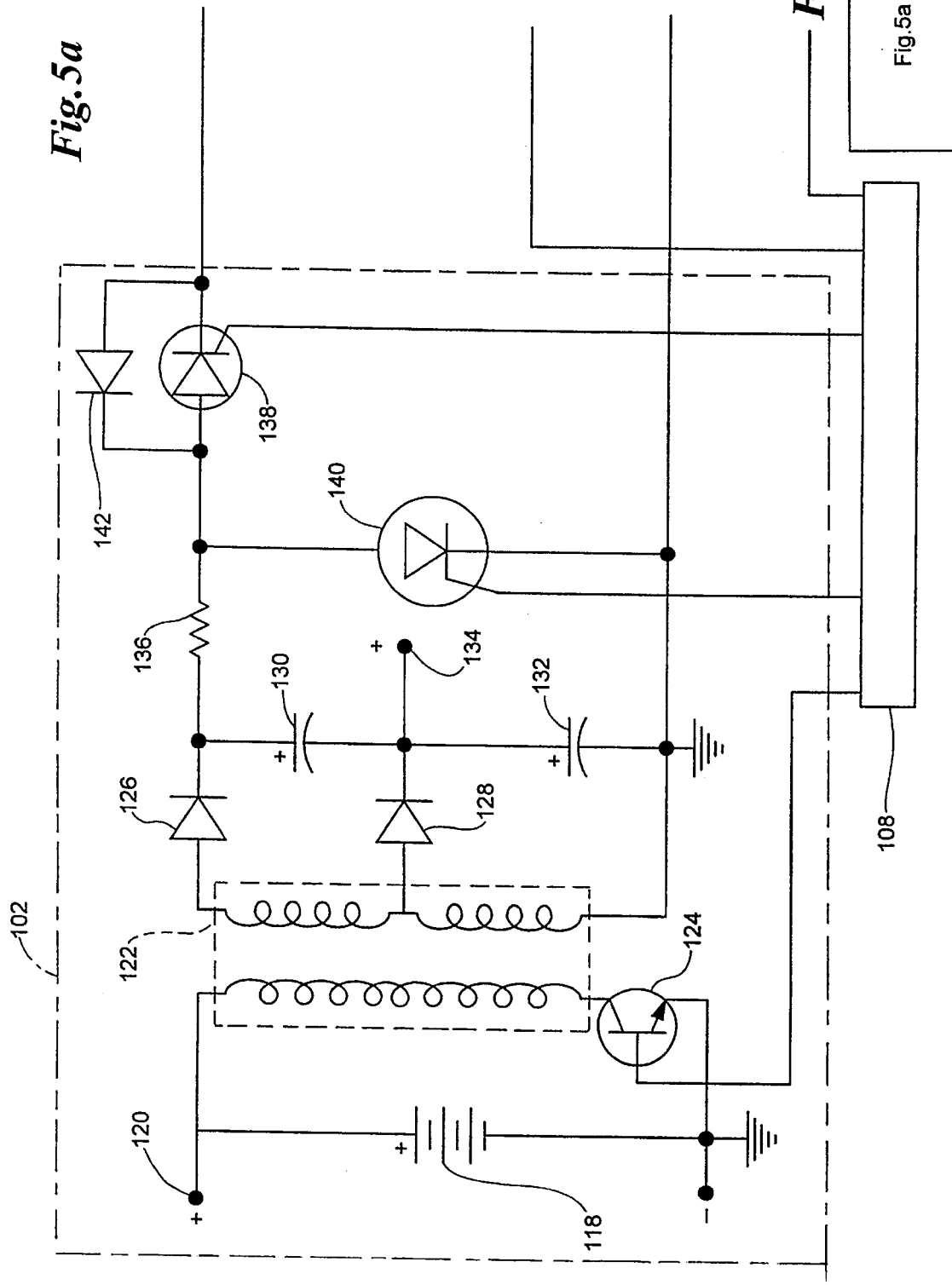

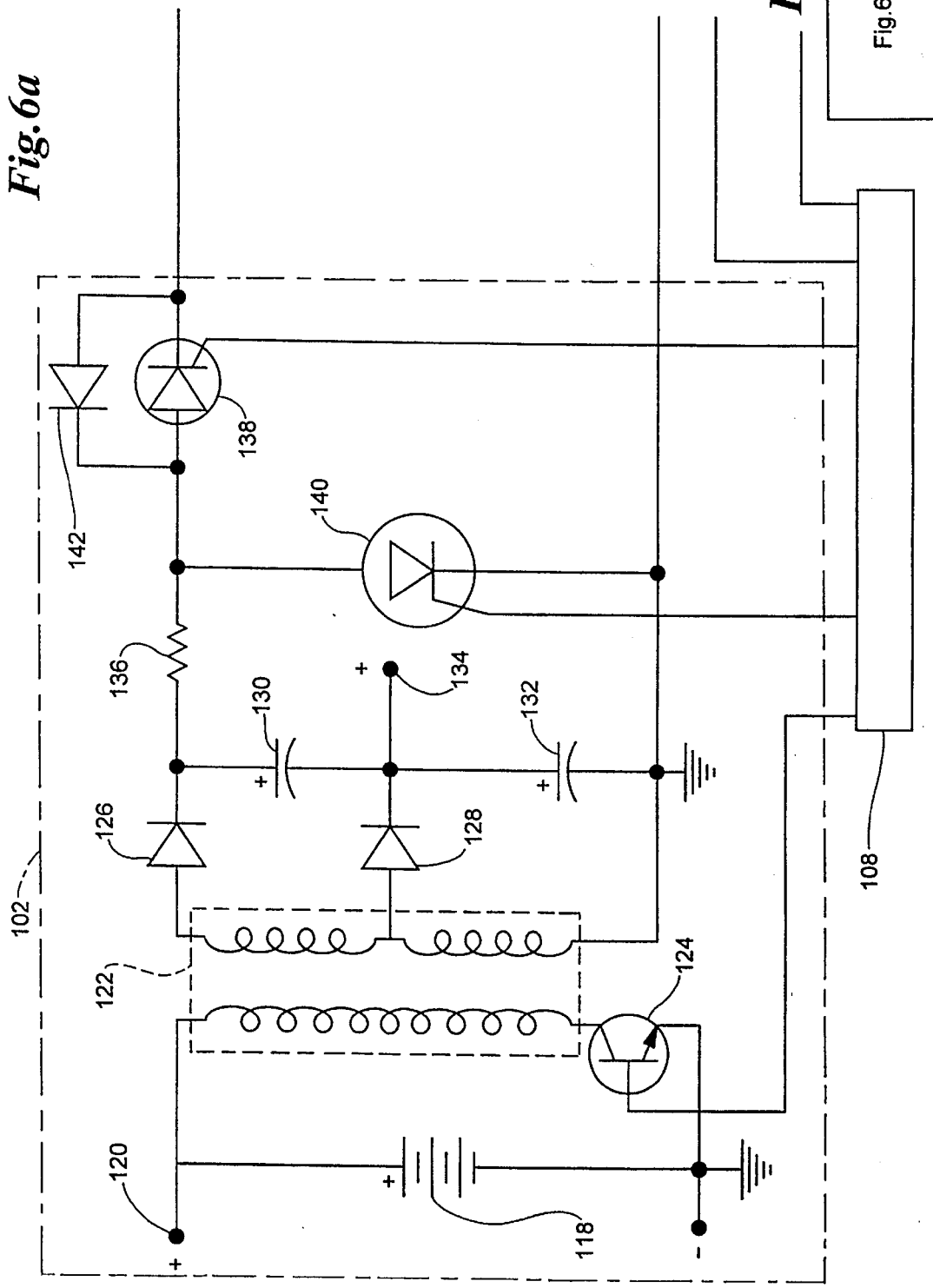

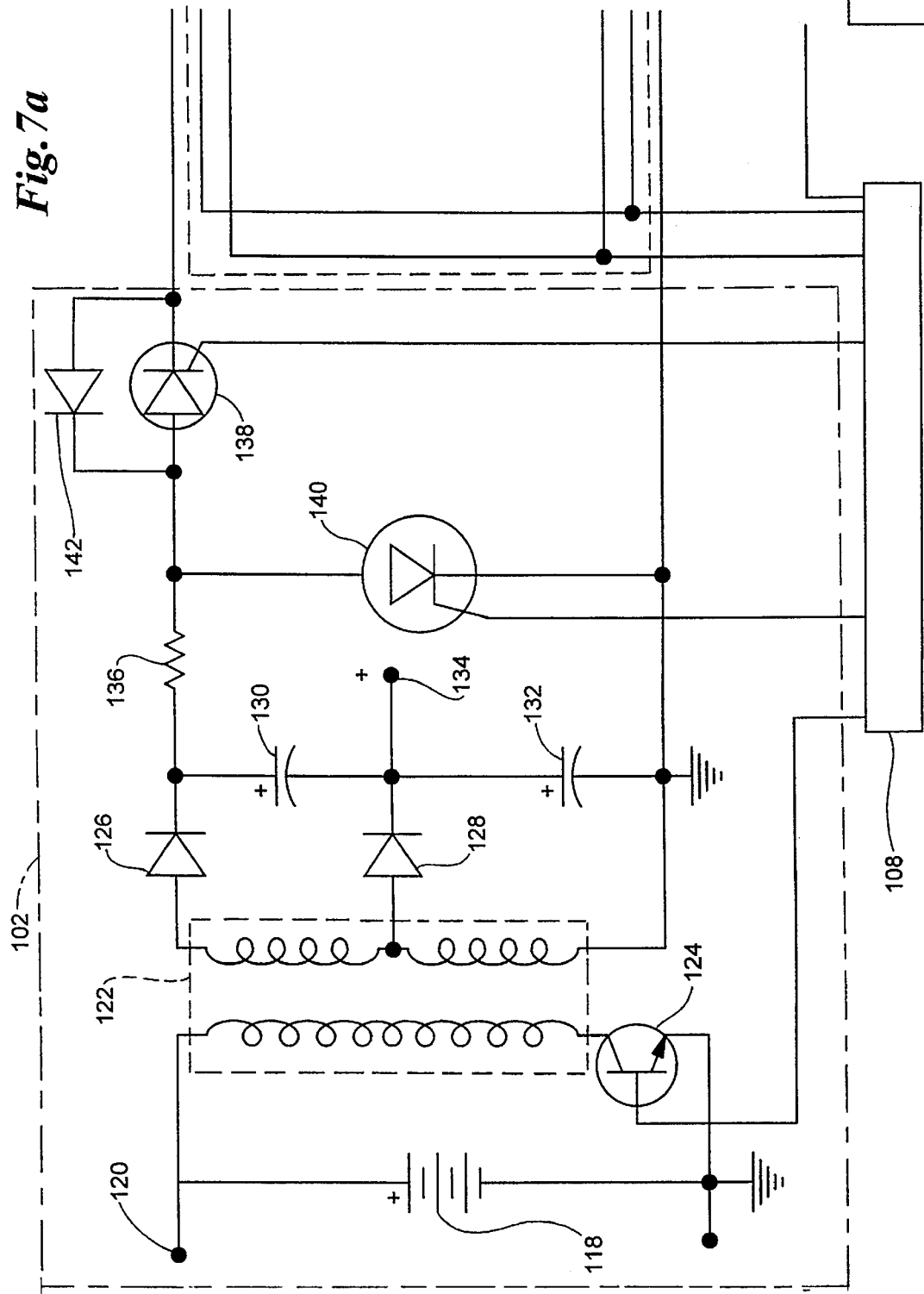

IMPLANTABLE DEFIBRILLATOR SYSTEM FOR GENERATING AN ACTIVE BIPHASIC WAVEFORM

FIELD OF THE INVENTION

The present invention relates generally to implantable defibrillator systems, and more particularly, to a method and apparatus for generating biphasic waveforms with an implantable defibrillator system.

BACKGROUND OF THE INVENTION

Implantable defibrillator systems deliver a high voltage electrical countershock to the heart in an attempt to correct or convert a detected cardiac arrhythmia or fibrillation. Due to the limitations on size and power imposed by the fact that these systems must be self-contained implantable devices, all existing implantable defibrillator systems generate an electrical countershock by charging a capacitor system to a high voltage from a low voltage battery and oscillator circuit. The battery is then switched out of the circuit and the electrical charge stored in the capacitor system is delivered as a truncated capacitive discharge through two or more implanted electrodes.

To date, there have been two basic kinds of discharge waveforms which have been used with implantable defibrillator systems: monophasic waveforms and biphasic waveforms; both of which are delivered as a truncated capacitive discharge. Monophasic waveforms are comprised of a single monotonically decaying electrical pulse that is typically truncated before the capacitor system is completely discharged. Biphasic waveforms, on the other hand, are comprised of a decaying electrical pulse that has a pair of decaying electrical phases that are of opposite polarity. To generate a biphasic pulse an H-bridge switch circuit connected to the electrodes is used to switch the polarity of the two phases. In generating the biphasic pulse, a first phase is discharged from the capacitor system, much in the same manner as a monophasic pulse. At the point in time that the first pulse is truncated, the H-bridge switch circuit immediately reverses the discharge polarity of the capacitor system as seen by the electrodes to produce the second phase of the biphasic waveform that is of the opposite polarity. A typical example of the use of an H-bridge circuit to generate a biphasic waveform in an implantable defibrillator system is shown in U.S. Pat. No. 4,998,531.

Over the last twenty five years, it has been demonstrated that appropriately truncated biphasic waveforms can achieve defibrillation with significantly lower currents, voltages and energies than monophasic waveforms of similar durations. Kroll, M W et al., "Decline in Defibrillation Thresholds", *PACE* 1993; 16#1:213–217; Bardy, G H et al., "A Prospective Randomized Evaluation of Biphasic vs. Monophasic Waveform Pulses on Defibrillation Efficiency in Humans", *J American College of Cardiology,* 1989; 14:728–733; and Wyse, D G et al., "Comparison of Biphasic and Monophasic Shocks for Defibrillation using a Non-Thoracotomy System", *American J Cardiology* 1993; 71:197–202. These findings are of particular importance for implantable devices because of the direct relationship between the amount of energy required for defibrillation and the overall size of the implantable device, i.e., the lower the energy required for defibrillation, the smaller the device.

Numerous theories have been advanced to explain the improved efficiency of the biphasic waveform over the more conventional monophasic waveform. Although some of these theories may partly explain, or may act cooperatively to explain, the effect a biphasic waveform has on the heart, there is currently no single accepted theory which fully explains the advantages of the biphasic waveform over the monophasic waveform. As a result, there is little or no agreement on what factors might further improve the efficiency and operation of the biphasic waveform.

In terms of the circuitry used to generate biphasic waveforms, the conventional H-bridge switch circuit has proven to be the only circuit used to generate biphasic waveforms in existing manufactured implantable cardioverter defibrillator (ICD) systems. Unfortunately, the switching components required for the conventional H-bridge circuit have several drawbacks. First, there is some question as to the long-term reliability of the switching components when used for this application. Second, the switching components are relatively large and their use tends to decrease the space in the ICD system that would otherwise be available for batteries or capacitors.

In addition, the use of the conventional H-bridge circuit requires a capacitor system that will have sufficient residual charge after truncation of the first phase to adequately power the second phase of the biphasic pulse. With existing ICD systems, all of which have capacitor systems with effective capacitance values of 140 µf or greater, this has not been a problem. The capacitor system is charged from a low voltage to high voltage energy converting system using a battery and flyback transformer combination oscillated at high frequency by a switching means and rectified to place a high voltage charge on the capacitor system. When sufficient energy has been stored, the energy converting system is turned off prior to delivery of the biphasic defibrillation pulse. As ICD systems are developed with smaller capacitance values, however, the amount of residual charge left in the capacitor system may not be sufficient to adequately power the second phase of the biphasic pulse.

The only other circuit design that has been proposed for generating biphasic waveforms arose out of the early theory that biphasic countershocks were more efficient because the net electrical charge transport was zero for a perfectly symmetrical biphasic waveform where the second phase was an exact mirror of the first phase. Schuder, J C et al. "Transthoracic Ventricular Defibrillation with Square-Wave Stimuli: One-Half Cycle, One Cycle and MultiCycle Waveforms", *Circulation Research,* 1964; 15:258–264. In recent experiments testing this theory, two identical capacitors were used to generate a "double capacitor" biphasic waveform in which a separate capacitor was used for each phase producing a symmetric biphasic waveform to ensure complete symmetry of the waveform. The results of these experiments established that mirror image dual capacitor systems were inferior to a single capacitor system in terms of producing lower &fibrillation threshold energies for symmetric biphasic waveforms. Kavanagh, K M et al., "Comparison of the Internal Defibrillation Thresholds for Monophasic and Double and Single Capacitor Biphasic Waveforms", *J American College of Cardiology,* 1989; 14:1343–1349; and Freeser, S A et al., "Strength-Duration and Probability of Success Curves for Defibrillation with Biphasic Waveforms", *Circulation,* 1990; 82:2128–2141.

While existing implantable defibrillator systems are capable of generating electrical countershocks that utilize the more efficient biphasic waveform, there presently is no single accepted theory for why the biphasic waveform is more efficient. This lack of an understanding of the nature and effect of the biphasic waveform has impeded further development and enhancement of the biphasic waveform.

Accordingly, it would be desirable to provide a method and apparatus for generating biphasic waveforms for an implantable defibrillator system that overcomes the disadvantages of the existing H-bridge circuitry. It would also be advantageous to improve on the methods and apparatus for generating biphasic waveforms as a result of an improved understanding of the nature and effect of the biphasic waveform on the fibrillating myocardium.

SUMMARY OF THE INVENTION

The present invention provides a method and apparatus for generating biphasic waveforms using an implantable cardioverter defibrillator that creates the second phase of the biphasic waveform from an active low energy source, rather than from a capacitive charge storage system. A high voltage first phase of the biphasic waveform is generated from the charge stored in a typical capacitive charge storage system. A low voltage second phase is generated from the continuous discharge of an active low voltage power source. By using an active low voltage power source system to directly produce the second phase of the biphasic waveform, the overall size and power requirements of the implantable device can be reduced.

Many theories have been offered for the improved efficacy of the biphasic defibrillation waveform. The present invention is derived from the use of a unique quantitative model based on the theory that the function of the first phase of the biphasic waveform is to synchronize the heart cells in the same manner as a conventional monophasic wave, and the function of the second phase is to remove any residual charge from the cell membranes that may have been deposited by the first phase of the countershock. The model used by the present invention assumes that the effective current requirement of the first phase is a linear function of the calculated residual (after the second phase) cell membrane voltage squared. The present invention uses this model to optimize the generation of biphasic waveforms for an implantable defibrillator having a first stage capacitance discharge and a second stage active low energy discharge.

In accordance with a first aspect of the present invention, an implantable cardioverter defibrillator apparatus discharges an active biphasic electrical countershock to an ailing human heart through at least two implantable electrodes located proximate the heart. The apparatus comprises an internal power source for providing electrical energy and a capacitance charge storage system, electrically connected between the power source and the electrodes, for generating a first phase of the biphasic countershock having a first polarity across the electrodes. The apparatus also includes inverter system, separate from the capacitance charge storage system and electrically connected between the power source and the electrodes, for generating a second phase of the biphasic countershock having a second and opposite polarity across the electrodes and drawing electrical energy directly from the power source during delivery of the second phase. A control means, operatively coupled to the power source, the capacitance charge storage system and the inverter system, controls the delivery of the first phase of the biphasic countershock from the capacitance charge storage system and the second phase of the biphasic countershock from the inverter system in response to a sensing of a cardiac dysrhythmia.

In accordance with a second aspect of the present invention, A method for operating an implantable cardioverter defibrillator device implanted within a human patient and electrically connected to at least two implantable electrodes located proximate a human heart to treat a cardiac arrhythmia delivers an active biphasic electrical countershock having a high voltage first phase and a low voltage second phase. The method comprises the device-implemented steps of sensing for a cardiac arrhythmia in a human patient and in response to a sensing of a cardiac arrhythmia, performing a series of substeps. The substeps include charging a capacitive charge storage system to a high voltage charge value using a low voltage power source and then discharging at least a portion of the charge value stored in the capacitive charge storage system through the electrodes to produce the high voltage first phase of the biphasic countershock. Next, the the low voltage second phase of the biphasic countershock is generated by using a continuous supply of low voltage electrical energy from the low voltage power source that is discharged through the electrodes to produce the second phase of the biphasic countershock having an opposite polarity from the first phase.

BRIEF DESCRIPTION OF THE DRAWINGS

FIGS. 5a and 5b is a more detailed circuit diagram of a preferred embodiment of the present invention.

FIGS. 6a and 5b is a more detailed circuit diagram of an alternative embodiment of the present invention.

DETAILED DESCRIPTION OF THE INVENTION

Figure 1:
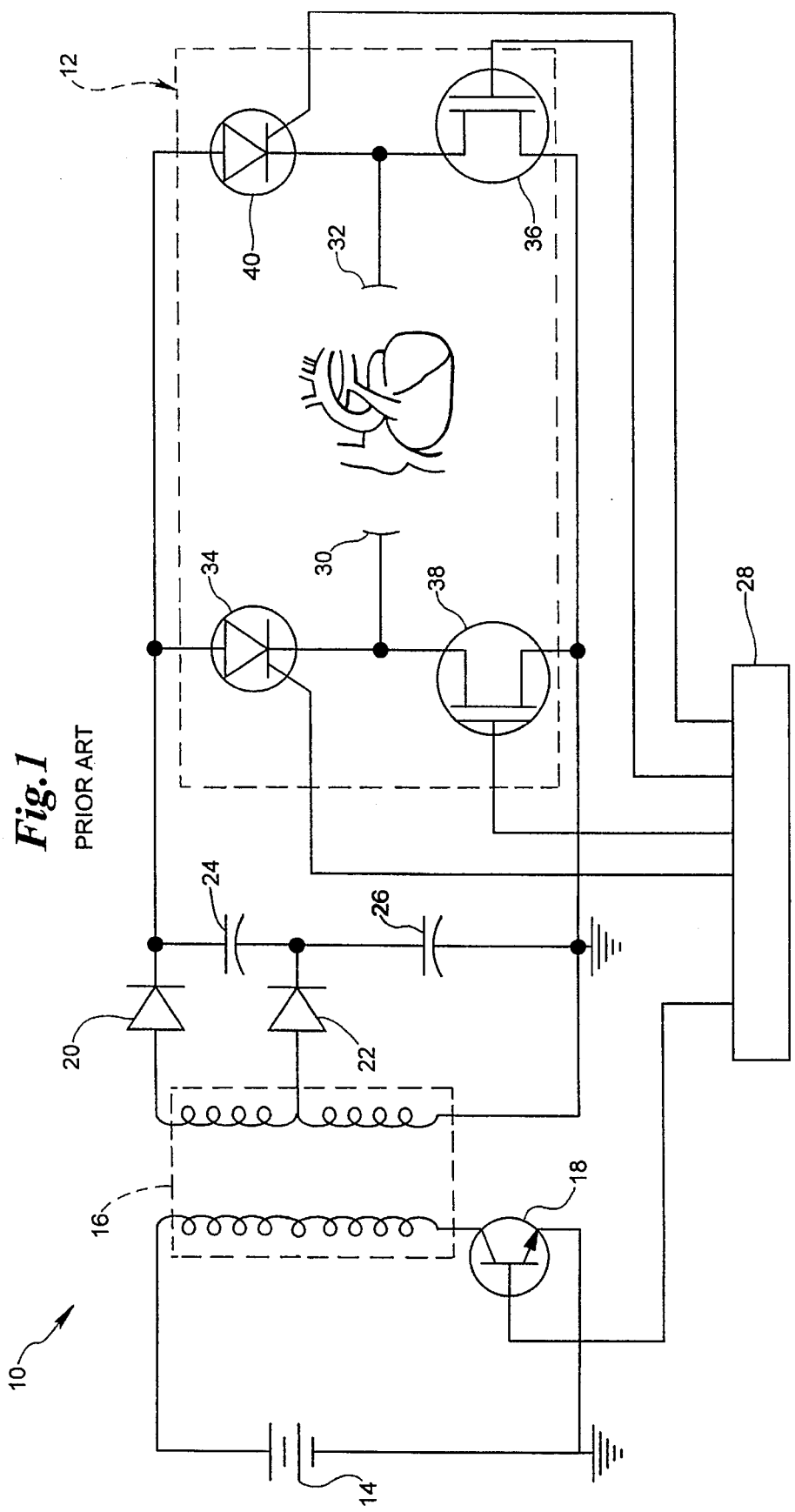
FIG. 1 is a schematic diagram of an ICD of the prior art.

In FIG. 1, a prior art example of an implantable cardioverter defibrillator (ICD) is depicted by circuitry 10 which includes an H-bridge 12, a battery power source 14, a double secondary fly back transformer 16, transistor switch 18 rectifying diodes 20, 22, high voltage storage capacitors 24, 26, circuit control 28, and cardiac electrodes 30, 32. H-bridge 12 includes switch 34, switch 36, switch 38, and switch 40.

Figure 2:
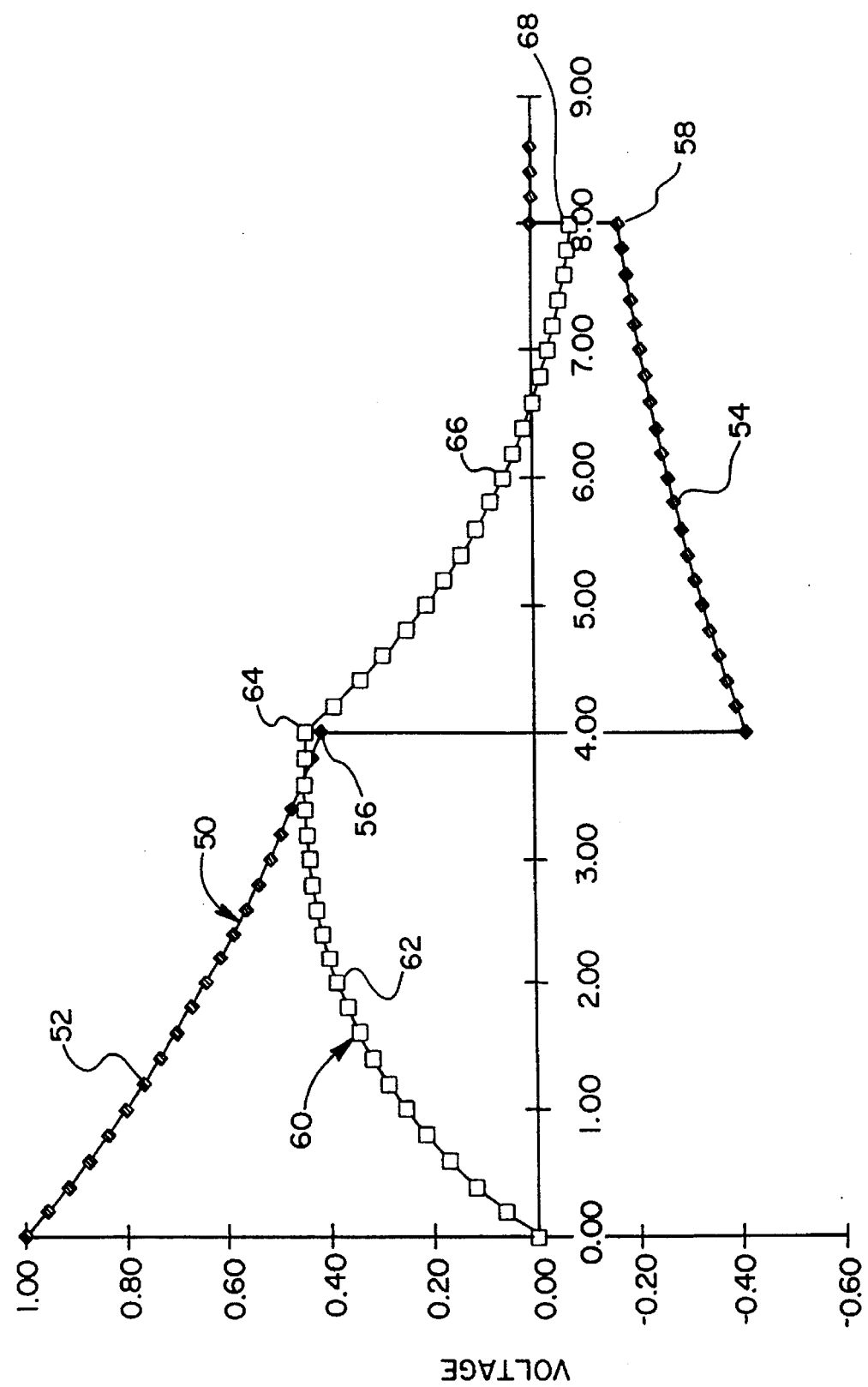
FIG. 2 depicts a representative voltage output for a biphasic waveform as generated by the ICD of FIG. 1.

A representative voltage output of the ICD circuit depicted in FIG. 1 is shown in FIG. 2. As shown in FIG. 2, output curve 50 has a upward first phase 52 and a downward second phase 54 with phase transition occurring at curve 56 and truncation of output at curve 58. A cell membrane voltage curve 60 is also shown in FIG. 2 depicting the cell membrane voltage response to the ICD output voltage shown in curve 50. A first phase curve 62 rises to transition 64 which corresponds to phase transition curve 56 at which time cell membrane voltage curve 60 enters a second phase 66 illustrating a decaying voltage to discharge truncation at 68.

Figure 3:
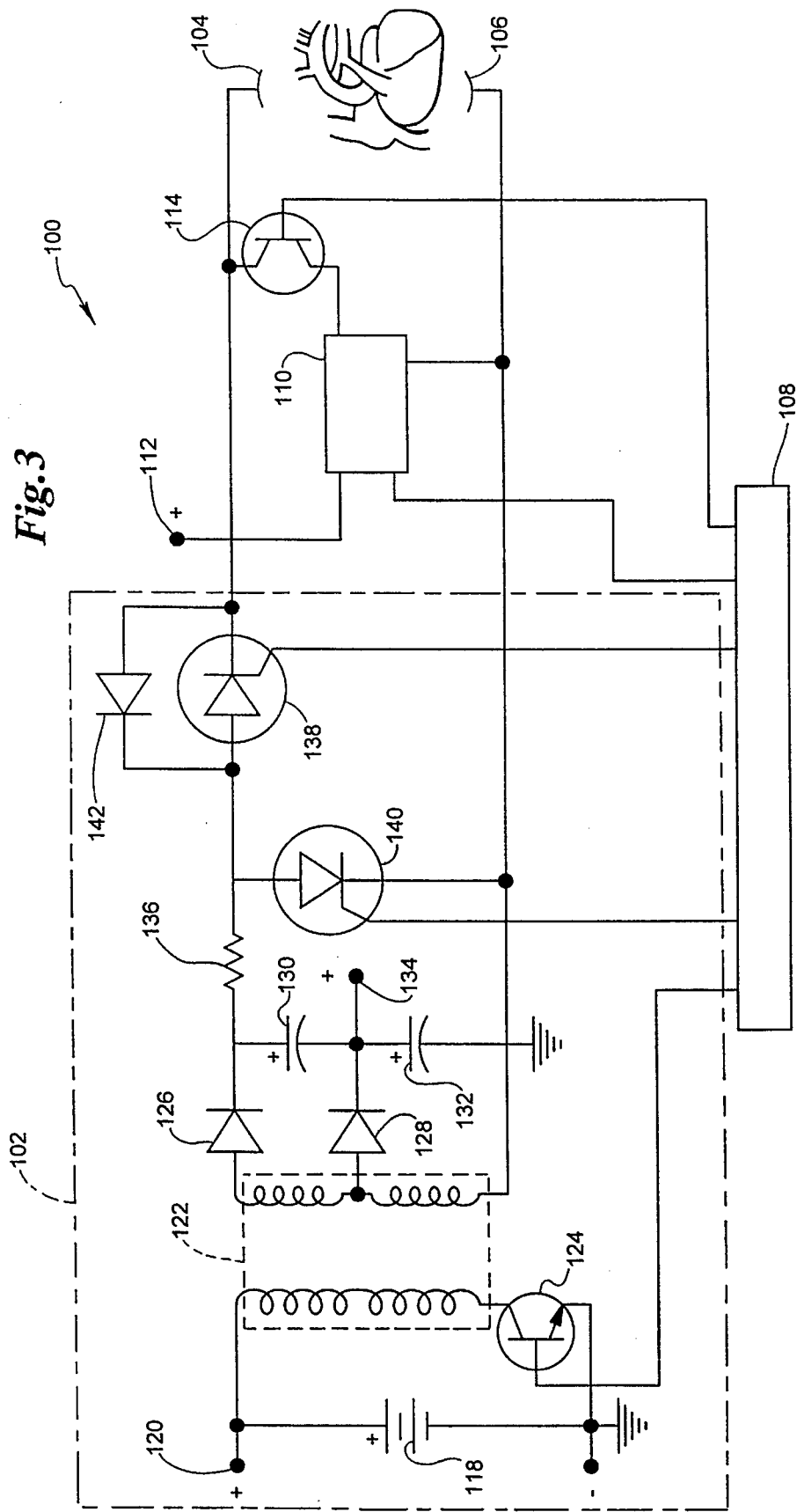
FIG. 3 is a schematic diagram of an ICD in accordance with the present invention.

Turning to FIG. 3 there is depicted an ICD 100 in accordance with the present invention comprising a high voltage output circuit 102, cardiac electrodes 104, 106, switch control 108, active low voltage output circuit 110, low voltage supply pin 112, and low voltage output switch 114. High output voltage circuit 102 includes a battery source 118 with a low voltage output pin 120, a flyback split winding transformer 122, an oscillating switch 124, rectifying diodes 126, 128, high voltage storage capacitors 130, 132, with intermediate voltage output pin 134, a load resistor 136, a discharge output switch 138, a discharge truncation switch 140, and a rectifying diode 142.

Figure 4:
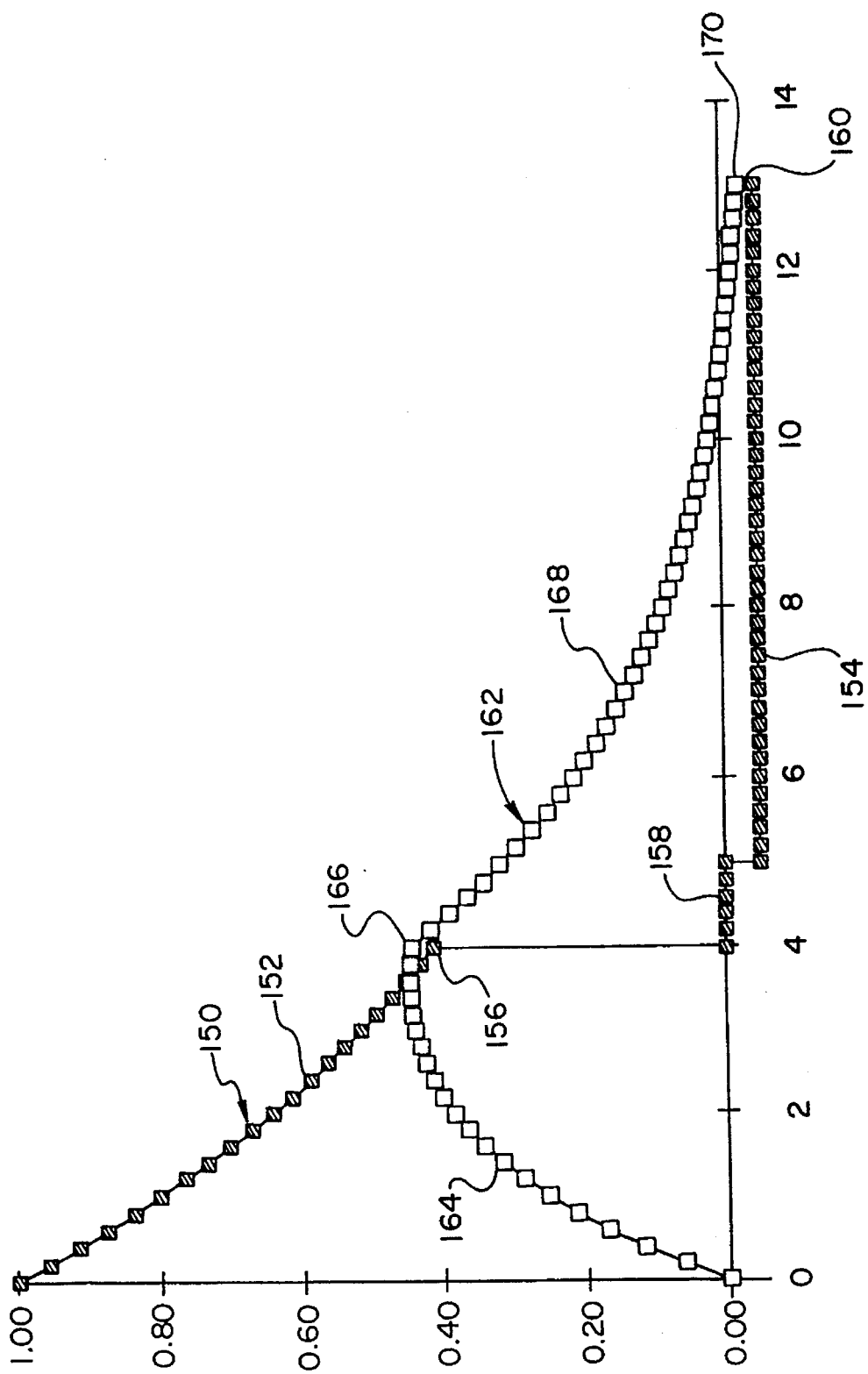
FIG. 4 depicts a representative voltage output for an active biphasic waveform as generated by the ICD of FIG. 3.

FIG. 4 discloses a representative output for an ICD for the present invention. As shown in FIG. 4, voltage output is characterized by curve 150 which includes a high voltage forward phase 152 and a low voltage opposite phase 154 separated by a transition period 158. High voltage curve 152 is truncated at curve 156 at which time it enters transition 158 with the entire biphasic waveform output ending at truncation 160. It will be appreciated that transition 158 may be either an extremely short transition (e.g., less than 100 μs) in which curve 156 is actively driven to a ground potential, or transition 158 may be a somewhat longer transition during which time curve 156 is allowed to float relative to a ground potential.

Also depicted in FIG. 4 is cell membrane voltage curve 162 illustrating the cell membrane voltage response to the output of an ICD of the present invention. Cell membrane curve 162 includes a forward phase rising voltage curve 164 that reverses its rise at 166 which corresponds to high voltage truncation 156 on curve 150. During the reverse phase 154 cell membrane curve 168 decreases to 170 which corresponds to truncation 160 when the discharge of the second phase is completed.

FIGS. 5a, 5b, 6a, 6b, 7a and 7b disclose three embodiments for active low voltage output circuit 110 in the present invention. Throughout these figures like numbers represent like components. In a preferred embodiment depicted in FIGS. 5a and 5b, an ICD 200 includes an active low voltage output circuit 110 comprising a transformer 202, an oscillating switch 204, a rectifying diode 206, and a smoothing capacitor 208.

Figure 6B:
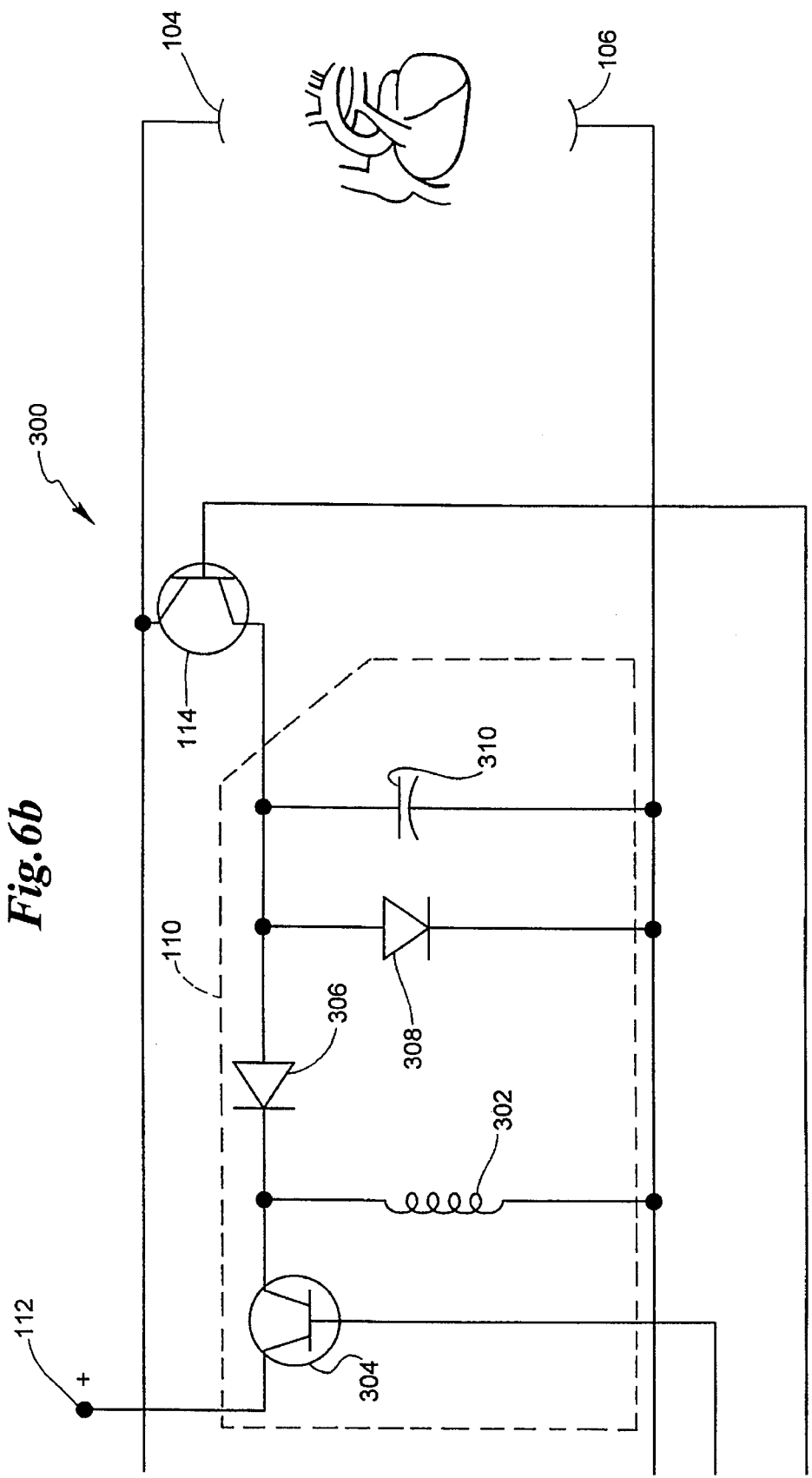

Another embodiment is disclosed in FIGS. 6a and 6b where active low voltage output circuit 110 includes an inductor coil 302, a low voltage switch 304, a rectifying diode 306, a zener diode 308, and smoothing capacitor 310.

Figure 7B:
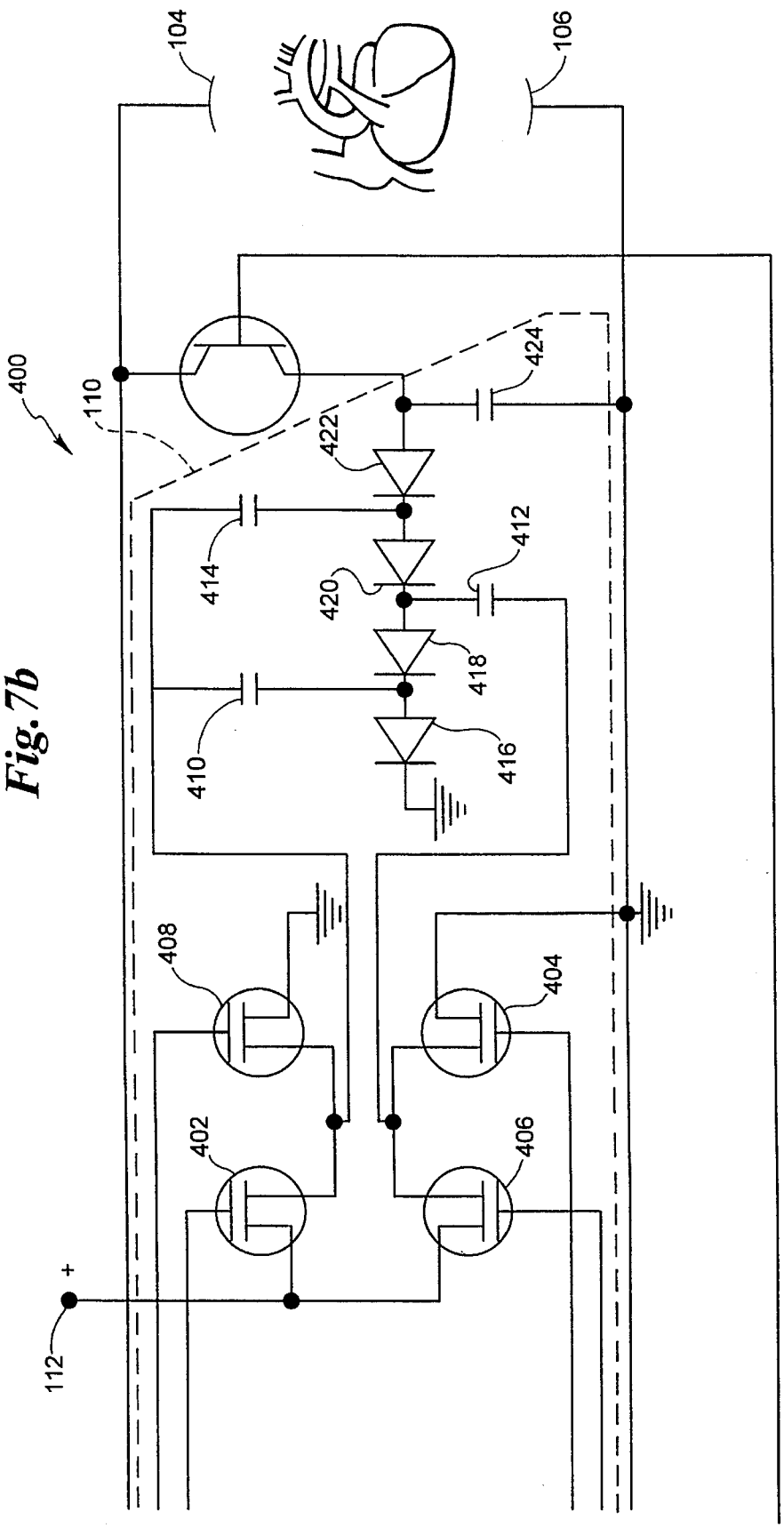
FIG. 7 is a more detailed circuit diagram of another alternative embodiment of the present invention.

An additional embodiment is disclosed in FIGS. 7a and 7b for an active low voltage output circuit 110 which includes switches 402, 404, 406, and 408, voltage storage capacitors 410, 412, and 414, rectifying diodes 416, 418, 420, and 422, and a smoothing capacitor 424.

In operation the invention as depicted in FIG. 3 generates the first phase curve 152 of output curve 150 as shown in FIG. 4 by way of circuit 102 in conjunction with switch control 108. High voltage output to cardiac electrodes 104, 106 is achieved in this initial phase where switch control 108 oscillates switch 124 at a high frequency supplying low voltage from battery 118 through the primary winding of transformer 122. The flyback secondary windings of transformer 122 generate a high voltage output which is rectified by diodes 126, 128 impressing a high voltage onto high voltage storage capacitors 130, 132. Once sufficient voltage has been stored on high voltage capacitors 130, 132 switch control 108 turns off switch 124 and the ICD 100 is now charged to deliver a high voltage first phase output to cardiac electrodes 104, 106. This high voltage first phase output is triggered by switch control means 108 activating high voltage switch 138 which is electrically connected in series with high voltage storage capacitors 130, 132, and resistor 136. Activation of switch 138 discharges high voltage storage capacitors 130, 132 across cardiac electrodes 104, 106. Switch control 108 allows the first phase discharge to continue until truncation point represented by 156 on curve 150 in FIG. 4. The high voltage discharge is terminated by switch control 108 activating switch 140 which acts essentially as a short across electrodes 104, 106 starving switch 138 of current turning off switch 138. Any residual capacitance effects electrodes 104, 106 is bled off through diode 142 to ground.

The second phase discharge represented by reverse phase curve 154 in FIG. 4 is generated by switch control 108 activating circuit 110 after transition period 158. The voltage circuit 110 is connected to low voltage supply 120 through pin 112. When circuit 110 is prepared to deliver an inverse phased discharge, switch control 108 activates switch 114 thereby supplying an inverted phase discharge of low voltage across cardiac electrodes 104, 106. At the end of this low voltage inverted discharge switch control 108 turns off switch 114 truncating the output of ICD 100 corresponding to discharge curve 160 in FIG. 4.

Figure 5B:
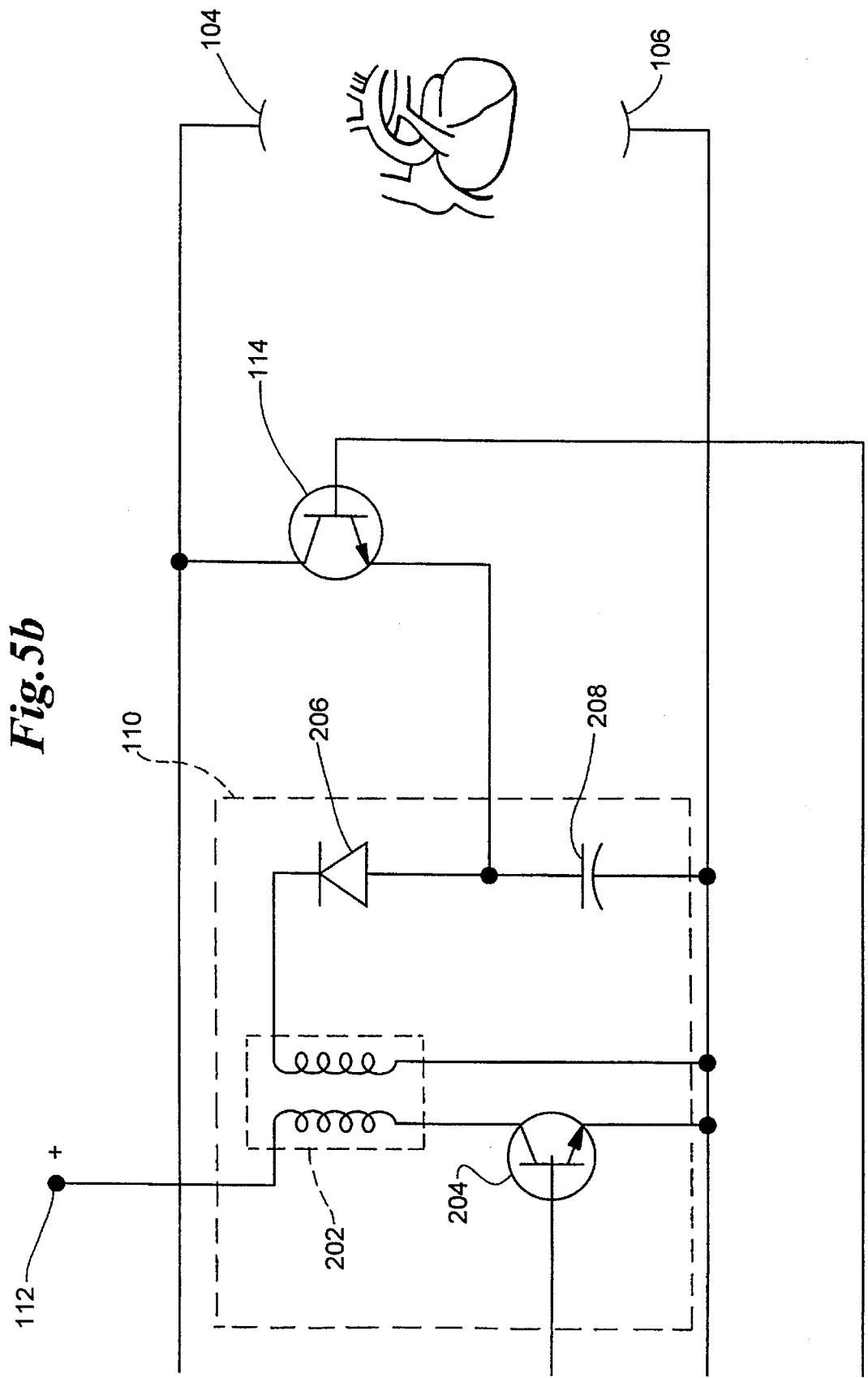

FIGS. 5a, 5b, 6a, 6b, 7a, 7b disclose in detail the components of low voltage inverting circuit 110. In FIGS. 5a and 5b, an ICD 200 comprises an active low voltage inverting circuit 110 where a transformer 202 has its primary windings connected to a low voltage pin 112 in series with a high frequency oscillating switch 204. When an inverted low voltage discharge is needed, switch control 108 activates high frequency oscillating switch 204 turning on circuit 110, the voltage generated by secondary windings of transformer 202 is rectified through diode 206 to supply a negative voltage at switch 114. The output of diode 206 is smoothed by capacitor 208 when switch control 108 activates switch 114 a negative voltage is delivered to electrode 104. During the entire time of this inverted low voltage output circuit 110 is active drawing current from low voltage pin 112. Pin 112 has two alternate connections, the first comprising a connection to low voltage pin 120 and drawing current directly from battery 118. An alternate connection is to connect pin 112 to intermediate voltage pin 134 drawing residual power from high voltage storage capacitor 132. With low voltage pin 112 connected to pin 120 transformer 202 may be appropriately sized to step up the voltage to that level desired.

The present invention anticipates supplying negative voltage as high as 30 to 50 volts across cardiac electrodes 104, 106. With pin 112 connected to pin 134, ICD 200 is able to efficiently utilize residual charge remaining on storage capacitor 132. At the point of truncation of the high voltage output at 156 in FIG. 4 the high voltage storage capacitors 130, 132 are disconnected from cardiac electrodes 104, 106 by turning off switch 138. Charge remaining on high voltage capacitors 130, 132 would otherwise be wasted and therefore is available for use in these second phase by drawing power at least from storage capacitor 132 into circuit 110. With pin 112 connected to pin 134 transformer 202 will be selected to receive the voltage from pin 134 and it is anticipated that the voltage supplied by storage capacitor 132 at this point would be higher than the voltage battery 118 would be capable of supplying. The inverted low voltage discharge is anticipated to require 50 volts or less therefore if voltage at 134 is higher than transformer 202 will be a step down transformer of appropriate size to meet the 50 volts or less range.

FIGS. 6a and 6b discloses an alternate embodiment of an ICD 300 where active circuit 110 uses inductor 302 as a ringing inductor. Switch control 108 activates switch 304 turning it on and off each time switch 304 is on. A certain amount of charge is stored in inductor 302 such that when switch 304 is turned off the charge stored in inductor 302 is discharged back into the circuit rectified by diode 306. This discharge is delivered to switch 114 as a multiplied voltage of the input from pin 112. Center diode 308 acts is a voltage limiter and in concert with capacitor 310 the negative voltage discharge to cardiac electrode 104 is limited to the appropriate voltage needed to carry out the inverted low voltage discharge. Capacitor 310 is chosen to help smooth out the discharge but is anticipated that the present invention does not need an absolutely smooth discharge in order to accomplish completion of a defibrillation treatment.

An additional alternate embodiment is disclosed in FIG. 7a and 7b as ICD system 400 where circuit 110 is arranged as a charge pump voltage multiplier. Low voltage pin 112 is connected to a sequence of switches 402, 404, 406, and 408 which are controlled alternately by switch control 108. When sequentially activated the switches deliver charge to capacitors 410, 412, and 414 in parallel. A sequence would include the following where switch control 108 would initially turn on switch 402 and switch 404 placing a charge in parallel across capacitors 410 and 414 and in series through diode 420 to capacitor 412. The next step would involve switch control 108 opening switches 402 and 404 enclosing switches 406 and 408. This sequentially on and off switch group 402 and 404 in sequence with switch group 406 and 408 in rapid succession places sufficient charge on capacitors 410, 412, and 414. It is calculated that the on/off sequence would need to repeat approximately 15 times to complete charge of capacitors 410, 412, and 414. When charging is completed switch control 108 then activates switch 114 allowing discharge of capacitors 410, 412, and 414 through the series of diodes 418, 420, and 422 to switch 114 and cardiac electrode 104 with a smoothing action from capacitor 424. This discharge of these capacitors is in effect a series discharge resulting in a voltage multiplying effect. For example, if pin 112 is connected to pin 120 and battery 18 is a six volt battery with a series of three capacitors 410, 412, and 414 the effective discharge voltage will be multiplied to 18 volts across cardiac electrodes 104 and 106.

The operation of the preferred embodiment will first review the standard waveforms for high voltage only capacitor system circuitry which is used to produce that waveform in existing ICD systems. With this background in mind, a review of the present biphasic theories, as well as the results of known experimental data on biphasic waveforms and defibrillation, is presented. Next, a new model for understanding biphasic waveforms is presented. The new model is then used to support the advantages of the active biphasic waveform generated by the ICD system of the present invention. For an ICD system having a single capacitor system, the model utilized by the present invention predicts that the duration of the second phase should be a constant value of about 1.5 to 4.0 ms, and optimally about 2.5 ms, for the range of presently encountered ICD capacitances and electrode resistances

PRESENT DIPHASIC THEORIES

Many theories have been proposed to explain the improved efficacy of the biphasic waveform. Several of these may be relevant and may in fact act jointly. To date, the following general theories have been advanced in the literature: (1) zero net charge transfer; (2) current summing; (3) sodium channel reactivation; (4) shortening of the refractory period; (5) lowering of the impedance; (6) improved energy delivery; and (7) change in the critical point. Each of these theories will be briefly summarized to contrast them with the theory employed by the present invention.

(1) Zero Net Charge Transfer

The feature of a one cycle bi-directional shock is that the net electrical transport is zero. Schuder J C, Stoeckle E H, Dolan A M, "Transthoracic Ventricular Defibrillation with Square-Wave Stimuli: One-Half Cycle, One Cycle, and MultiCycle Waveforms", *Circulation Research* 1964; 15:258–264. A recent study found a negative correlation between the charge contents in each phase of efficient biphasic shocks of a certain design. Walker R G, Walcott G P, Swanson D K, et.al., "Relationship of Charge Distribution between Phases in Biphasic Waveforms", *Circulation* 1992; 86 No. 4:I-792 (Abstract). This would imply that a zero net charge transfer was not required or necessarily efficient, and that a zero net charge transfer (at least at the electrode level) may not be important for the efficacy of a biphasic waveform.

(2) Current Summing

It has also been suggested that when the second phase of a biphasic pulse is removed, thereby creating a monophasic pulse, it is necessary to increase the discharge voltage of this pulse so that the current amplitude would be equal to the sum of current values of 2 first half periods for the discharge. Consequently, the capacity of the heart to summate the stimulation effect of both phases of current may be utilized for reduction of the defibrillating current in one direction and for decreasing the hazard of injury to the heart by a strong current. Gurvish N L, Markarychev, V A: "Defibrillation of the Heart with Biphasic Electrical Impulses", *Kardiologilia* 1967; 7:109–112. See also Tchou P, Krum D, Aktar M, Avitall B, "Reduction of Defibrillation Energy Requirements with new Biphasic Waveforms", *PACE* 1990; 13:507 (Abstract). However, this theory does not explain the sensitivity of the biphasic efficiency to the duration of the second phase.

(3) Reactivation of the Sodium Channels

It has been suggested that the first phase of the biphasic waveform serves as a conditioning prepulse which helps to restore sodium channel activation in preparation for the excitation by the second phase. Jones J L, Jones R E, Balasky G, "Improved Cardiac Cell Excitation with Symmetrical Biphasic Defibrillator Waveforms", *American J Physiology* 1987;253:H1418–H1424. This reactivation hypothesis was given additional support and a theoretical underpinning in a later paper which demonstrated that a hyperpolarizing prepulse did reactivate additional sodium channels thus promoting increased excitability. Kavanagh K M, Duff H J, Clark R, et.al., "Monophasic vs. Biphasic Cardiac Stimulation: Mechanism of Decreased Energy Requirements", *PACE* 1990:13;1268–1276. This theory may explain why the biphasic wave prolong refractoriness after the shock. Swartz J F, Jones J L, Jones R E, Fletcher R D, "Conditioning Prepulse of Biphasic Defibrillator Waveforms Enhances Refractoriness to Fibrillation Wavefronts", *Circulation Research* 1991;68:438–449. Unfortunately, this enhanced stimulation effect is very dependent on waveform duration. Karasik P, Jones R, Jones J., "Effect of Waveform Duration on Refractory Period Extension Produced by Monophasic and Biphasic Defibrillator Waveforms", *PACE* 1991;14:715 (Abstract). Thus, the reactivation theory for biphasic waveforms may or may not be important depending upon the importance of the extension of refractory period vs. synchronization as the fundamental basis of defibrillation.

(4) First Phase Shortening of Refractory Period

It has been long known that a hyperpolarizing pulse delivered during phase 2 of the action potential can shorten the refractory period, thus, allowing a depolarizing pulse to more easily activate the cell, and it has been suggested that this mechanism could explain the increased effectiveness of the biphasic shock. Tang A S L, Yabe S, Wharton J M, et.al., "Ventricular Defibrillation Using Biphasic Waveforms: The Importance of Phasic Defibrillation", *J American College of Cardiology* 1989;13:207–14. This proposed theory is similar to the sodium channel reactivation hypothesis and the cited literature may apply in both cases.

(5) Lower Impedance

There is some evidence that the average current of a pulse is the best measure of its effectiveness (for a given pulse duration). Bourland J D, Tacker W A, Geddes L A. et al., "Comparative Efficacy of Damped Sign Wave and Square Wave Current for Transchest Ventricular Defibrillation in Animals", *Medical Instrumentation* 1978;12#1:38–41. Thus, for a given voltage in a waveform, one would expect that the waveform with the lowest impedance would be the most efficacious. It has been found that the average impedance of the second phase of a biphasic waveform is significantly lower than that of the first phase. Tang A S L, Yabe S, Wharton J M, et.al., "Ventricular Defibrillation Using Biphasic Waveforms: The Importance of Phasic Defibrillation", *J American College of Cardiology* 1989;13:207–14. The lower impedance theory, however, is suspect for two reasons. First, the reductions in required voltage are found to be lower than the impedance reductions and, as a result, the current requirement is itself reduced for the biphasic waveform. Second, the impedance reduction results from the transition between the phases and thus only benefits the second phase of the shock. As a result, the lower impedance theory does not explain the overall improvements in efficacy which have been observed for the biphasic waveform.

(6) Improved Energy Delivery

It has been suggested that the increased efficacy of the biphasic waveform is due to its ability to deliver a larger fraction of the energy in the capacitor for a typical capacitive discharge defibrillator. U.S. Pat. No. 4,850,357, issued to Bach and entitled "Biphasic Pulse Generator for an Implantable Defibrillator". Clearly one could deliver more of the energy in a capacitor by merely increasing the duration of the pulse, but this has been shown to be deleterious in that long durations can lower the average current and thereby decrease efficiency. Kroll M W, Adams T P, "The Optimum Pulse Width for the Implantable Defibrillator", 7th Purdue Conference on Defibrillation, *American Heart Journal* 1992;124#3:835 (Abstract).

For general stimulation and defibrillation, it has been shown that pulses significantly wider than the appropriate chronaxie time use energy inefficiently. Irnich W, "The Chronaxie Time and its Practical Importance", *PACE* 1980;8:870–888. By delivering the energy in two shorter phases, one could utilize the energy without the penalty of the increased duration. A reasonably efficient capacitive discharge monophasic waveform will deliver nearly 90% of the capacitor's energy with an efficient pulse duration. By use of the biphasic waveform one can thus deliver another 10% of the energy. However the energy reductions reported, for biphasic usage, are significantly greater than 10%. It has also been shown that, for a more optimal duration, the stored energy requirements were also lowered with the biphasic waveform. Swartz J F, Karasik P E, Donofrio J, et.al., "Effect of Biphasic Waveform Tilt on Human Non-Thoracotomy Defibrillation Threshold", *PACE* 1993;16#4II:888 (Abstract). Thus, the argument that the increased benefit of biphasic waveforms might lie from increasing the percentage of energy delivered can certainly not account for all of the effects which have been observed.

(7) Differences in the Critical Point

It has been suggested that differences in the critical point of the biphasic waveform may explain its advantage over the monophasic waveform. Ideker R E, Tang A S L, Frazier D W, et.al., "Ventricular Defibrillation: Basic Concepts", *Cardiac Pacing and Electrophysiology* 3rd Ed., edited by El-Sherif N & Samatt, W B Saunders Co. Philadelphia 1991;42:713–726. Re-entry may be induced when a sufficient potential gradient exists that is at an angle (e.g., perpendicular) to the dispersion of refractoriness. This has been shown to exist with a shock field of 5 V/cm in tissue just recovering from its effective refractory period. Frazier D W, Wolf P D, Wharton J M, et.al., "A Stimulus Induced Critical Point: A Mechanism for Electrical Initiation of Re-Entry in Normal Canine Myocardium", *J of Clinical Investigation* 1989;83:1039. According to this theory, it is thought, because these potential gradients exceeding the critical value can cause unidirectional block and prolongation of refractoriness, there is a lower critical point. If the biphasic shock has a lower critical point, then there is less of a chance of refibrillation from the shock. It has been shown, however, that the first reactivation following an unsuccessful countershock is typically found in the region with the lowest gradient, not the highest. Shibata N, Chen P S, Dixon E G, et. al., "Epicardial Activation After Unsuccessful Defibrillation Shocks in Dogs", *American J Physiology* 1988;255:H902–H909.

SPECIFIC EXPERIMENTAL FINDINGS ON BIPHASIC WAVEFORMS

There are several specific findings which should be considered. Most importantly, these experimental findings should be explainable by any putative theory of the biphasic waveform advantage. These specific findings are: (1) the biphasic wave generates fewer post shock arrhythmias; (2) a symmetric biphasic offers minimal or no benefit; (3) the second phase duration for a single capacitor shock should be shorter than the first duration; and (4) there is less benefit with the biphasic waveform for transthoracic defibrillation.

(1) Biphasic Waveform has Fewer Post Shock Arrhythmias

There are several reports that the biphasic waveform has fewer post shock arrhythmias than does the monophasic waveform for shocks of equal strength. This is certainly true for shocks near their threshold levels. This was first noted in the early Schuder paper, above, and was confirmed in a recent study with dogs. Zhou X, Daubert J P, Wolf P D, et al., "Epicardial Mapping of Ventricular Defibrillation With Monophasic and Biphasic Shocks in Dogs", *Circulation Research* 1993;72:145–160. When the duration of the post shock arrhythmias is measured by detecting the contraction arrest time, it has been shown that the arrest time for rectangular biphasic waveforms with optimal durations could be reduced to half of the arrest time associated with monophasic waveforms of similar strength. Jones J L, Jones R E, "Decreased Defibrillator-Induced Dysfunction with Biphasic Rectangular Waveforms", *American J Physiology* 1984;247:H792–H796.

(2) Symmetric Biphasic Offer Little or No Benefit

A study of isolated perfused canine hearts using symmetrical biphasic pulses—each phase had an identical amplitude and durations of 5 ms—showed no advantage in the threshold energy for defibrillation. It was found that the symmetric biphasic waveform also offered no advantage in minimizing myocardial depression at any multiple of the defibrillation threshold current. Niebauer M J, Babbs C F, Geddes L A, et.al., "Efficacy and Safety of the Reciprocal Pulse Defibrillator Current Waveform", *Medical and Biological Engineering and Computing* 1984;22:28–31.

As previously discussed in the background section, similar results were obtained with a "double capacitor" biphasic waveform in which a separate capacitor was used for each phase to ensure symmetry. Kavanagh K M, Tang A S L, Rollins D L, et.al., "Comparison of the Internal Defibrillation Thresholds for Monophasic and Double and Single Capacitor Biphasic Waveforms", *J American College of Cardiology* 1989;14:1343–1349. Another example that symmetric biphasic waveforms offer no advantage is a study that used a single capacitor waveform of 7 ms which had a threshold of 1.19 J, while the symmetric dual capacitor waveform with both the first and second phase each being 7 ms had a 1.99 J threshold. Feeser S A, Tang A S L, Kavanagh K M, et.al., "Strength—Duration and Probability of Success Curves for Defibrillation with Biphasic Waveforms", *Circulation* 1990;82:2128–2141.

(3) Efficient Biphasic Has Phase 2 Shorter than Phase 1

In a study done with a right ventricular catheter and a subcutaneous patch in dogs, single capacitor biphasic waveforms for which the first phase was 50, 75, and 90% of the total duration had a lower defibrillation energy threshold than a monophasic waveform of the same total duration. However for waveforms in which the second phase had 75 or 90% of the total duration the energy requirements increased significantly. Chapman P D, Vetter J W, Souza J J, et.al., "Comparative Efficacy of Monophasic and Biphasic Truncated Exponential Shocks for Nonthoracotomy Internal Defibrillation in Dogs", *J American College of Cardiology* 1988;12:739–745.

Similar results were found in dogs with epicardial patch electrodes in which a total of 25 combinations of first and second phase durations were studied. In all cases in which the second phase duration was shorter than the first phase duration, the total energy required was lower than that of a monophasic wave whose duration was equal to the first phase duration of the biphasic wave. Conversely, in all cases in which the second phase duration was greater than the first phase, the energy requirements were increased over the comparable monophasic waveform. Feeser S A, Tang A S L, Kavanagh K M, et.al., "Strength—Duration and Probability of Success Curves for Defibrillation with Biphasic Waveforms", *Circulation* 1990;82:2128–2141.

Still another canine study using both epicardial and pericardial patches found that the single capacitor biphasic waveforms with the lowest energy thresholds had a second phase shorter than the first phase. As with the other studies, those shocks with the second phase longer than the first phase had thresholds greater than that of comparable monophasic waveforms. Dixon E F, Tangas L, Wolf P D, Meador J T, Fine M G, Calfee R V, Ideker R E, "Improved Defibrillation Thresholds with Large Contoured Epicardial Electrodes and Biphasic Waveforms", *Circulation* 1987;76:1176–1184.

(4) Biphasic Waveform Has Less Transthoracic Advantage

Another canine study compared monophasic and biphasic thresholds for both internal and external defibrillations. While the biphasic waveforms had energy thresholds that were approximately one half of those of the monophasic waveforms for internal defibrillation, the advantages of the biphasic waveform in external defibrillation were usually not statistically significant when comparing waveforms of similar durations. Johnson E E, Hagler J A, Alferness C A, et al., "Efficacy of Monophasic and Biphasic Truncated Exponential Shocks for Nonthoracotomy Internal Defibrillation in Dogs", *J American College of Cardiology* 1988;12:739–745.

DEFIBRILLATION AT THE CELLULAR AND TISSUE LEVEL

While defibrillation is presently understood fairly well at the cellular and tissue level for monophasic waveforms, there is as yet no general understanding at the cellular and tissue level for biphasic waveforms.

Monophasic Waveform at the Cellular and Tissue Level

There is now strong evidence, from optical recordings, that the monophasic shock defibrillates by resynchronizing a large majority (i.e., at least 90%) of the myocardial cells. Dillon S M, "Synchronized Depolarization after Defibrillation Shocks: A Possible Component of the Defibrillation Process Demonstrated by Optical Recordings in Rabbit Heart", *Circulation* 1992;85:1865–1878. The requirement that a monophasic countershock resynchronize the large majority of myocardial cells is apparently due to the fact that a defibrillation strength shock will not only stimulate recovered cells, i.e. those in phase 4, but will also extend the activation potential of those already activated cells. This has been supported by non optical measurements showing that monophasic defibrillation shocks are indeed capable of extending the refractory period of activated cells in dogs, Sweeney R J, Gill R M, Steinberg M I, et.al., "Ventricular Refractory Period Extension Caused by Defibrillation Shocks", *Circulation* 1990;82:965–972; and humans, Belz M K, Speery R E, Wood M A, Ellenbogen K A, Stambler B S, "Successful Defibrillation Prolongs Action Potential Durations in Humans", *PACE* 993;16:932 (Abstract).

These results have created two semantic problems. First, it is now clear that the "absolute refractory" period is not absolutely refractory. It merely requires defibrillation strength shocks for stimulation. The second problem lies with the use of the word "stimulation". Stimulation has been traditionally used (in the narrow sense) as referring to electrical initiation of a new activation potential by opening the voltage gated sodium channels. While it appears that activation potential prolongation is indeed initiated by reopening the sodium channels, this is not characteristic of conventional pacing stimulation, for example. To minimize confusion, the present invention will use the term "countershock stimulation" in reference to cell stimulation in a defibrillation context.

The difference between conventional pacing stimulation and countershock stimulation may help to partially explain the nature of the defibrillation process. For example, the chronaxie time for far-field stimulation (in the conventional pacing sense) is on the order of 1 ms. Frazier D W, Krassowska W et al., "Extracellular Field Required for Excitation in Three-Dimensional Anisotropic Canine Myocardium.", *Circulation Research* 1988;63:147–164. The chronaxie time for the monophasic defibrillation pulse, on the other hand, has been consistently found to be in a range of 2–4 ms. Wessale J L, Bourland J D, Tacker W A, et al, "Bipolar catheter defibrillation in dogs using trapezoidal waveforms of various tilts", *J Electrocardiology* 1980; 13 (4):359–366; Niebauer M J, Babbs C F, Geddes L A, et al, "Efficacy and safety of defibrillation with rectangular waves of 2 to 20 milliseconds duration", *Crit. Care Medicine* 1983; 11 #2:95–98. A critical part of the defibrillation synchronization may be the countershock stimulation occurring in the refractory period. The increased difficulty of countershock stimulation in the so-called absolute refractory period may explain why the chronaxie time is increased from around 1 ms for pacing stimulation to around 3 ms for countershock stimulation.

Biphasic Waveform at the Cellular and Tissue Level

The exact mechanisms of biphasic defibrillation are not generally understood. Several qualitative findings exist, however, that, when properly interpreted, may give guidance towards an understanding of its mechanisms. These are that the biphasic waveform: (1) is an inferior stimulator compared to the monophasic waveform; (2) has less of a refractory period prolongation; and (3) has less post shock arrhythmias.

Biphasic is an Inferior Stimulator

Animal studies have compared the stimulation biphasic waveforms to that of monophasic waveforms and found that a biphasic pacing waveform required increased stimulus currents in relative refractory tissue, Wharton J M, Richard V J, Murry C E, et.al. "Electrophysiological Effects In Vivo of Monophasic and Biphasic Stimuli in Normal and Infarcted Dogs", *PACE* 1990;13:1158–1172; and that a biphasic defibrillation Waveform was less effective in countershock stimulating partially refractory myocardium. Daubert J P, Frazier D W, Wolf P D, et.al. "Response of Relatively Refractory Canine Myocardium to Monophasic and Biphasic Shocks", *Circulation* 1991;84:2522–2538.

Biphasic has Smaller Refractory Period

Another animal study measured the activation potential prolongation from a shock delivered at a 50% repolarization point. A symmetric biphasic waveform was compared to monophasic waveforms. The biphasic waveform was able to generate a significantly smaller action potential prolongation for equal voltage shocks. Zhou X, Knisley S B, Wolf P D, et.al., "Prolongation of Repolarization Time by Electric Field Stimulation with Monophasic and Biphasic Shocks in Open Chest Dogs", *Circulation Research* 1991;68:1761–1767.

Biphasic has Fewer Post Shock Arrhythmias

It has been already mentioned that the biphasic waveform generates less post shock arrhythmias. It has also been shown that the conduction block is less severe for the biphasic wave versus the monophasic wave and, for equal strength shocks, persists for less time. Yabe S, Smith W M, Daubert J P, et.al., "Conduction Disturbances Caused by High Current Density Electric Fields", *Circulation Research* 1990;66:1190–1203.

NEW MODEL FOR BIPHASIC WAVEFORMS

There is still no clear explanation for why the biphasic waveform is more efficient that the monophasic waveform. Consequently, there is no clear guidance on how, or even if, improvements can be made to the generation and delivery of biphasic waveforms. The present invention offers a model for the biphasic waveform that appears to explain why an active energy second phase delivery of a biphasic waveform in accordance with the present invention is more efficacious than the existing technique of delivering biphasic waveforms from a single capacitor system.

The model that is utilized by the present invention is that the second phase of the biphasic waveform (when optimally sized) serves to remove the excess charge remaining on the cell membrane from the first phase. It is hypothesized that the excess charge remaining on cells after the countershock stimulation may end up creating a new arrhythmia some time after the countershock stimulation. Consequently, for a monophasic shock to be successful, it must not only capture enough cells to halt fibrillation, but it must also capture enough cells so that no post shock arrhythmias will occur as a result of the excess charge remaining on the cell membrane. In other words, by having the second phase of a biphasic countershock return the cell membrane potentials to their pre-shock potential, there are fewer post shock arrhythmias, and, because there are fewer post shock arrhythmias, fewer cells need to be synchronized by the first phase. In addition, the protective refractory period extension requirement may be reduced. It is theorized that these two factors may explain the reduced amplitude requirements for the first phase.

The circuit model of the cell that is implicit in this discussion is essentially the standard capacitive membrane coupled to resistive paths giving a membrane time constant. Fozzard H A, "Membrane Capacity of the Cardiac Purkinje Fiber", *J Physiol* (Great Britain) 1966;182:255–267. In this model, $V_e$ represents the voltage across the defibrillation electrodes and $V_m$ represents the voltage across the membrane. The exact values of the resistances and capacitance are not important, the salient feature is the resulting membrane time constant which will be called $\tau_m$.

Referring again to FIG. 2, the voltages are shown as a function of time which would be expected in such a model for a biphasic waveform delivered from an existing ICD system having a single capacitor system. Assuming an ICD capacitance of 150 µF and an electrode resistance of 50 Ω, the electrode voltages will be as shown for a biphasic wave, with each phase having a duration of 3.5 ms. For ease of notation, the remaining discussion will refer to the duration of the a biphasic waveform in a shorthand form as "3.5/3.5", indicating that the first phase is 3.5 ms and the second phase is 3.5 ms. The capacitor voltages 51 and 53 for the first and second phases of the waveform 50 are shown beginning at a normalized value of 1.00 volts. The membrane voltages 60 are calculated with the use of a representative time constant of the non-Purkinje ventricular cell membrane of approximately 3 ms. Weidmann S, "Electrical Constants of Trabecular Muscle from Mammalian Heart", *J Physiol* (Great Britain) 1970; 210: 1041–1054.

The exact transmembrane potential of an individual cell as shown in FIG. 1 is not relevant for this analysis. What is important is the perturbation, by the first phase 52 of the defibrillation countershock, of the membrane voltage 60 from its existing value. The model of the biphasic waveform utilized by the present invention suggests that the cancellation of this perturbation, i.e. the "burping" of the membrane charge, appears to be the critical function of the second phase. As can be seen from FIG. 2, at the end of the second phase, the transmembrane potential has been left, in this case, with a negative perturbation potential 63 as a result of the delivery of the biphasic waveform, instead of the desired zero perturbation potential which is the goal of the theory of the present invention.

The membrane voltage $V_m$ is calculated as a fraction of the maximum potential attainable for an infinitely long rectangular pulse at the electrodes. The absolute value of the potential (in volts) is not critical as the return to zero is the sole goal of the biphasic waveform in accordance with the theory of the present invention. During the defibrillation shock the electric field will charge areas of the cell membrane positively, some negatively, and some not at all. Knisley S B, Blitchington T F, Hill B C, "Optical Measurement of Transmembrane Potential Changes During Electric Field Stimulation of Ventricular Cells", *Circulation Research* 1993;72:255–270. Also, depending upon the location of the cells vis-à-vis the electrodes, the actual membrane voltage will vary significantly. Using a normalized value (i.e. a fraction) for $V_m$ allows the model to concentrate on the simple goal of returning the membrane voltage to a zero perturbation.

A quantitative model for the present invention can be determined using a model for discussing the effects of a countershock on the myocardium. The myocardium has resistance and capacitance characteristics, but the exact values of the resistances and capacitance are not important. The relative contribution to the time constant of the series resistances and the shunt resistances (from the so called leaky-capacitor model) is also not important. The salient feature is the resulting myocardial cell membrane time constant which will be called $\tau_m$. $V_e$ represents the voltage across defibrillation electrodes, and $V_m$ represents the voltage across the cell membrane.

The analysis begins by temporarily ignoring the circuitry of the ICD and eliminating the resistance in parallel with the membrane capacitance in favor of simplicity. This parallel (leaky membrane) resistance may be ignored if $R_m$ is taken as the Thevenin equivalent of two resistors. Thus, $R_m$ and $C_m$ are the membrane series resistance and capacitance respectively. As before, the node $V_e$ represents the voltage between the electrodes, while $V_m$ denotes the voltage across the cell membrane. Nodal analysis provides an equation for the solution of $V_m$:

$$C_m \frac{dV_m}{dt} + \frac{V_m - V_e}{R_m} = 0. \tag{1}$$

Rearranging equation 1 to solve for $V_e$, we have $$V_e = V_m + (R_m C_m)\frac{dV_m}{dt}. \tag{2}$$

The discharge of a single capacitor in such a circuit is well-known and modeled by $$V_e = e^{(-t/R_s C_s)}$$

and so may be placed into equation 2 to give:

$$\tau_m \frac{dV_m}{dt} + V_m = e^{(-t/\tau_s)}, \tag{3}$$

where $\tau_m = R_m C_m$ represents the time constant of the myocardial cell in the circuit model, and $\tau_s = R_s C_s$ represents the time constant of the defibrillator shock in the circuit model. This differential equation models the effects of a monophasic, time-truncated, capacitor-discharge defibrillator on the myocardium.

Equation 3 is a first-order linear differential equation, and may be written as $$\frac{dV_m}{dt} + \left(\frac{1}{\tau_m}\right)V_m = \left(\frac{1}{\tau_m}\right)e^{(-t/\tau_s)}. \tag{4}$$

In the form of equation 4, the general solution is $$V_m = e^{-t/\tau_m}\left(\int\left(e^{t/\tau_m}\left(\frac{1}{\tau_m}\right)e^{-t/\tau_s}\right)dt + c\right). \tag{5}$$

where c is an integration constant. Integrating equation 5 and simplifying the resultant expression, we have for the membrane voltage at the end of the first phase:

$$V_{m_1}(t) = ce^{-t/\tau_m} + \frac{\tau_s}{\tau_s - \tau_m} e^{-t/\tau_s}. \tag{6}$$

To determine the constant of integration c, we assume the initial value for $V_m$ to be $V_{m1}(0)=0$. Applying the initial condition to equation 6, we have $$c = -\frac{\tau_s}{\tau_s - \tau_m}.$$

Therefore, the solution to our initial-value problem for phase 1 is $$V_{m_1}(t) = \frac{\tau_s}{\tau_s - \tau_m}(e^{-t/\tau_s} - e^{-t/\tau_m}). \tag{7}$$

A biphasic waveform reverses the flow of current through the myocardium during the second phase. A simplified model of the myocardial cell may again be used by merely reversing the flow of current in the circuit model by changing the sign on the shock current. We thus derive an almost identical differential equation to equation 3 above. The difference is the sign on the right hand side:

$$\tau_m \frac{dV_m}{dt} + V_m = -e^{(-t/\tau_s)}. \tag{8}$$

At the beginning of phase 1, we assumed a normalized value of 1 for the charge found on the capacitor at the time the defibrillation shock was initiated, so that equation 3 may be more explicitly written as $$\tau_m \frac{dV_m}{dt} + V_m = 1 \cdot e^{-t/\tau_s}.$$

At the beginning of phase 2, the capacitor has discharged for a period of time equal to the length of phase 1, and we shall denote this time period as $d_1$ (the duration of phase 1). The normalized capacitor charge at the start of phase 2 is therefore $e^{-d_1/\tau_d}<1$, and so equation 8 may be written more explicitly as $$\tau_m \frac{dV_m}{dt} + V_m = -e^{-d_1/\tau_s} \cdot e^{-t/\tau_s}. \tag{9}$$

Equation 9 is again a first-order linear differential equation, and we write this equation in the form below to apply standard methods for determining its solution:

$$\frac{dV_m}{dt} + \left(\frac{1}{\tau_m}\right)V_m = -\left(\frac{1}{\tau_m}\right) \cdot e^{-d_1/\tau_s} \cdot e^{-t/\tau_s}. \tag{10}$$

In the form of equation 10, the general solution is $$V_{m_2}(t) = ce^{-t/\tau_m} - \frac{\tau_s}{\tau_s - \tau_m} \cdot e^{-d_1/\tau_s} \cdot e^{-t/\tau_s}. \tag{11}$$

To determine the constant of integration c, we note that at the end of phase 1 the (initial) value for $V_{m2}$ is $$V_{m_2}(0) = V_{m_1}(d_1) = \frac{\tau_s}{\tau_s - \tau_m}(e^{-d_1/\tau_s} - e^{-d_1/\tau_m}).$$

Applying the initial condition to equation 11, we have $$c = \frac{\tau_s}{\tau_s - \tau_m} K_m$$

where $$K_m = 2e^{-d_1/\tau_s} - e^{-d_1/\tau_m}.$$

Therefore, the solution to the initial-value problem for phase 2 is $$V_{m_2}(t) = -\frac{\tau_s}{\tau_s - \tau_m} (K_s e^{-t/\tau_s} - K_m e^{-t/\tau_m}) \quad (12)$$

where $$K_s = e^{-d_1/\tau_s}$$

which may be rewritten as:

$$V_{m_2} = \left[\frac{\tau_s}{\tau_s - \tau_m}\right] [(2e^{-d_1/\tau_s} - e^{-d_1/\tau_m})e^{-d_2/\tau_m} - e^{-d_1/\tau_s} e^{-d_2/\tau_s}] \quad (13)$$

The requirement defining an optimal pulse duration for phase 2 is that the phase 2 pulse leave as little residual membrane potential remaining on a non-depolarized cell as possible. Equation 12 provides a means to calculate the residual membrane potential at the end of the second phase for those cells that did not depolarize. To determine the optimal phase 2 pulse duration, we set equation 12 equal to zero and solve for t. This optimal pulse duration for phase 2, then, is $d_2$. To begin, we have $$0 = -\frac{\tau_s}{\tau_s - \tau_m} (K_s e^{-t/\tau_s} - K_m e^{-t/\tau_m}).$$

Because $(\tau_s/(\tau_s - \tau_m))$ cannot be zero, we solve for t using the equation $$0 = K_m e^{-t/\tau_m} - K_s e^{-t/\tau_s}.$$

Arranging the exponential functions onto the left hand side, we get $$\frac{e^{-t/\tau_s}}{e^{-t/\tau_m}} = \frac{K_m}{K_s}. \quad (14)$$

Taking the logarithm of each side, solving for t, and rearranging terms, we get $$t = \left(\frac{\tau_s \tau_m}{\tau_s - \tau_m}\right) \cdot \ln\left(\frac{K_m}{K_s}\right) \quad (15)$$

and $$d_2 = \left[\frac{\tau_s \tau_m}{\tau_s - \tau_m}\right] \cdot \ln\left\{2 - \left[\frac{e^{-d_1/\tau_m}}{e^{-d_1/\tau_s}}\right]\right\}. \quad (16)$$

For typical values of a 140 μF capacitor and a 50 Ω electrode resistance the time constant $(\tau_s)$ will be 7 ms. Assume that $\tau_m$ is the membrane time constant. The durations of the two phases will be referred to as $d_1$ and $d_2$ respectively. The membrane potential at the end of phase one will be given by Equation 7 as $$V_{m1} = (\tau_s/(\tau_s - \tau_m)) [(e^{-d_1/\tau_s} - e^{-d_1/\tau_m})$$

The subtraction of the two exponentials represents the attempt by the discharge capacitor of the ICD (as represented by the positive term with time constant $\tau_s$) to charge the membrane while the membrane capacitance is resisting the charging with its electrical inertia (as represented by the negative term containing $\tau_m$).

The membrane voltage at the end of the second phase is given as the following equation rearranged from Equation 12:

$$V_{m2} = (\tau_s/(\tau_s - \tau_m))[(2e^{-d_1/\tau_s} - e^{-d_1/\tau_m})e^{-d_2/\tau_m} - e^{-d_1/\tau_s} e^{-d_2/\tau}]$$

This intimidating equation is necessary to reflect the interaction between the two phase durations and two the time constants.

The fundamental hypothesis of the model of the present invention is that a low residual membrane voltage lowers the electrical requirements of the first phase. The lower residual membrane voltage, as a result of the second phase of the shock, reduces the necessary current of phase one that would otherwise be required to extinguish the additional local arrhythmias caused by the higher residual membrane voltage.

The electrical content of the first phase could be represented in many fashions. To correct for varied durations, the "effective" current model is used as set forth in Kroll, M W, et al., "Decline in Defibrillation Thresholds", *PACE* 1993; 16#1:213–317. The effective current is simply the average current divided by the "duration correction". The effective current is also equal to the rheobase current for shocks exactly at the threshold level. The function of the duration correction is to normalize the average current for the higher requirements of narrower pulses which is given by the strength duration curve.

The duration correction is:

$$1 + (d_{cr}/d)$$

and thus the effective current is given by:

$$I_{eff} = I_{ave}/[1 + (d_{cr}/d)]$$

The model of the present invention predicts that the required effective current has a minimum value which will be referred to as $I_o$ for a perfectly shaped biphasic wave leaving a zero residual membrane potential. The model then further predicts that the increase in required effective current from this $I_o$ value is proportional to the excess membrane potential squared. In other words:

$$I_{eff} = I_o + k V_m^2.$$

APPLICATION OF THE NEW MODEL

To begin with, the new model will be applied to the known characteristics and experimental results of biphasic waveforms to see whether the model accurately predicts these.

Explanation of the Minimal Benefit of the Symmetrical Waveform

As observed earlier, biphasic waveforms with symmetrical phases have been shown to offer minimal or no benefit—certainly for defibrillation thresholds in terms of energy (as opposed to a square-wave voltage). An analysis of FIG. 2 explains why this result might be seen in the animal model and in this quantitative model. To approximate a symmetrical biphasic waveform a large capacitor (2000 μF) and a 50 Ω electrode is assumed. A 5/5 ms biphasic waveform is then produced. Note that the two phases are fairly symmetric. The cell membrane voltage is noted to rise to about 0.75 during the first phase and then fall rapidly during the second phase. Because the current flow is reversed between the phases, the cell membrane is discharged more rapidly during this second phase than it was charged during the first phase. Therefore the cell voltage is "pulled through" zero during the second phase and is left at a high negative potential of about 0.5. This potential is ⅔ as large in magnitude as that which was found at the end of the first phase.

As can be seen, the second phase did not serve to remove residual cell voltage—but rather served primarily to change its polarity. The present model suggests that there is no advantage in having a mere polarity change in the residual cell voltage 63. Thus the symmetric biphasic should have only a minimal advantage over the monophasic waveform for defibrillation thresholds.

Model Explanation for Benefit of a Shorter Second Phase

As previously indicated, several earlier studies have shown that it is important that, at least in a single capacitor biphasic waveform, that the duration of the second phase be less than or equal to the duration of the first phase. The equations given earlier can be solved to show the relationships between the two different phase durations. It can be directly shown, for reasonable electrode resistances and presently used capacitance values in a single capacitor system, that the second duration should be always smaller than the first—for the lowest threshold.

This finding can also be derived directly from the model more intuitively from a review of the membrane and electrode voltages in FIG. 2. Again the basic principal is that the discharge rate in the second phase is greater than the charge rate during the first phase. Therefore if the first phase was equal in amplitude and duration to the second phase the second phase would still leave a large reverse voltage membrane potential 63. This is true even for the unequal phase voltages seen with practical capacitor sizes.

Consider for example the 150 μF capacitor used for the example in FIGS. 1 and 2. Even though the capacitor is discharging at a sufficient rate so that the electrode voltage in the second phase is significantly lower than that of the first phase, the membrane discharge rate is still significantly greater in phase two. The membrane capacitance was charged for 3.5 ms during the first phase. A close inspection in FIG. 2 shows that the membrane capacitance would be fully discharged in a little over 2 ms of the second phase. If the second phase was equal in duration to the first phase (i.e. total duration=7 ms) then the membrane potential would be seen to be negative and thus non optimal. However, that negative potential would still be closer to zero than that which would have occurred with no second phase (i.e. with a 3.5 ms monophasic waveform). For this reason single capacitor waveforms in which both phases are equal still offer benefits over the monophasic waveforms. Nevertheless, they are not the optimal biphasic waveform for presently used capacitor values. As taught by the present invention, however, this is not true for smaller, and possibly more optimal, values of capacitances.

Model Explanation for the Reduced Transthoracic Advantage Transthoracic defibrillation may produce a more symmetrical distribution of current and potential gradients in the heart than is found with epicardial defibrillation. This would imply that the ratio of minimum to maximum fields is much lower with transthoracic defibrillation than it is with epicardial defibrillation. Therefore, with a shock of sufficient strength to synchronize the overwhelming majority of the heart, there is a much lower likelihood of a substantial mass of cells being partially stimulated and with pro-arrhythmic residual charges. Thus, the "burping" action of the second phase would act on a much smaller population of cells for the transthoracic case than it would for the epicardial defibrillation case. This would reduce the benefit of the second phase and hence of the biphasic wave itself.

Deleterious Effects of the Residual Charge

The residual charge may interfere with defibrillation at two extremes. In the first case the excessive field will leave a charge on the membrane which is intrinsically harmful and proarrhythmic. In the second case a borderline stimulation field will fail to assertively capture and hence synchronize the cell. For both of these cases an implicit hypothesis of the model of this invention is that (at least some) of the deleterious effects of the shock are prevented or minimized by immediately removing the residual charge left by the shock.

Direct experimental data supporting this hypothesis is limited. It is accepted that repolarizing current pulses will reduce the incidence of early after depolarizations. January C T, Shorofsky S., "Early After depolarizations: Newer Insights into Cellular Mechanisms", *J Cardiovascular Electrophysiology* 1990;1:161–169. Indirect evidence in favor of the second effect (borderline stimulation) was found in studies that showed that the first reactivation, following an unsuccessful monophasic shock, is in the area that had received the smallest electrical field. Shibata N, Chen P S, Dixon E G, et. al., "Epicardial Activation After Unsuccessful Defibrillation Shocks in Dogs", *American J Physiology* 1988;255:H902–H909; Chen P S, Shibata N, Dixon E G. "Activation During Ventricular Defibrillation in Open-Chest Dogs", *J Clinical Investigation* 1986;77:810–823. Despite these results, the authors of these two studies concluded, "These findings suggested that the shock extinguished all of the activation fronts present during fibrillation, but, after a latency period, the shock itself gave rise to new activation fronts that caused fibrillation to be reinitiated." This conclusion is inapposite to the model of the present invention which concludes that it is the excess charge on the cell membranes, and not the shock itself, that would give rise to new activation fronts that would cause post shock arrhythmias.

Effects of Borderline Fields

As previously indicated, one of the possible consequences of the model of the present invention is an explanation of the borderline field phenomenon. The Hodgkin-Huxley model of invitro cell propagation that, when the local response has almost reached propagating size, it becomes unstable and varies from shock to shock. Hodgkin A L, "The Subthreshold Potentials in Crustacean Nerve Fibre", *Proc. Roayl Society,* 1938, 126:87–121. Using the Hodgkin-Huxley model, computer estimates of stimulation strength-duration curves have shown that ". . . a highly unstable subthreshold propagating wave is initiated in principle by a just threshold stimulus." Cooley J W, Dodge F A., "Digital Computer Solutions for Excitation and Propagation of the Nerve Impulse", *Biophysical Journal* 1966;6:583–599. Four different cellular models have also been studied with borderline strength stimulation, and all four models showed similar activation delays possible of 20, 12, ">20," and 8 ms respectively. Krassowska W, Cabo C, Knisley S B, et.al., "Propagation vs. Delayed Activation During Field Stimulation of Cardiac Muscle", *PACE* 1992;15:197–210. Latencies and other graded responses also have been experimentally observed in mammalian cardiac tissue. Kao C Y, Hoffman B F, "Graded and Decremental Response in Heart Muscle Fiber", *American J Physiology* 1958;194 (1):187–196.

The above results suggest an intriguing possibility extending from the present model. When the shock is delivered to the heart, at threshold, there are regions of the heart that will receive an insufficient field for countershock stimulation. In the transition zone between these non-stimulated cells and the stimulated cells, there will be cells that will receive a borderline stimulation of the type which has been analyzed by this model. These borderline stimulated cells would then be activated with a significant delay or an unstable response. This could be sufficient to destroy the synchronization desired from the defibrillation shock. The second phase of the defibrillation shock, by removing that residual charge, may be able to arrest the delayed and unstable responses. This would then eliminate this source of desynchronization.

APPLICATION OF THE MODEL TO ACTIVE LOW ENERGY DISCHARGE SYSTEMS

Referring again to FIGS. 5a and 5b, the first phase of a biphasic electrical countershock is generated from the discharge of a capacitive charge storage system in the usual manner. The second phase of the biphasic electrical countershock, however, is generated in a dramatically different manner. When switch 140 is enabled to truncate the first phase, diode 142 will conduct the cardiac electrode current in a reverse direction around SCR switch 138 due to the Helmholz capacitance of the cardiac electrodes 104, 106. The Helmholz capacitance is based on the separation of charges from the metal of the electrode being placed in an electrolyte with a voltage applied to the electrode. Although the Helmholz capacitance is a nonlinear funtion of voltage and is fairly complex to model, as a simplification it is possible to estimate the Helmholz capacitance for cardiac electrode 104 and 106 to be on the order of 10 μF when the cardiac electrode voltage is above about 20 V. When the cardiac electrode voltage is below about 20 V, then the current drawn to the cardiac electrode is relatively minor. This condition of SCR switch 140 short the cardiac electrodes 104 and 106 to ground through diode 142 is maintained for a period of time. During this period, the Helmolz capacitance of approximately 10 μF across the cardiac electrodes begins to discharge the cell membrane. In the discharge curve shown in FIG. 4, this duration is shown as a shorted electrodes region where the elcetrode votlage is seen to be fixed at 0 V as shown at transition 158. In this embodiment, the transition period 158 is approximately equal to 1 ms.

At the end of the shorted electrodes region, an active voltage is generated directly from power source 118 to provide the cell membrane discharge current. The active voltage is generated in any of the manners as previously described in connection with the detailed description of FIGS. 5a, 5b, 6a, 6b, 7a and 7b. The active voltage will be on the order of 15–25 V. A minimum voltage is required for the active voltage as the defibrillation electrodes 104 and 106 conduct current rather poorly below a voltage difference of about 10 V. On the other hand, maintaining active voltages of 30–40 V or greater across the cardiac electrodes 104 and 106 presents a significant power drain on power souce 118. Consequently, an optimal level for the active voltage of the present invention is between about 15–25 V. Such an active voltage level avoids both the problems of poor current conduction and high battery drain. The use of an active voltage source for the second phase of a biphasic electrical countershock also avoids the low voltage tails from a capacitive discharge which would otherwise require a higher initial discharge voltage or a shorter discharge duration.

I claim:

1. An implantable cardioverter defibrillator apparatus for discharging an active biphasic electrical countershock to an ailing human heart through at least two implantable electrodes located proximate the heart, the apparatus comprising:

an internal power source for providing electrical energy;

capacitance means, electrically connected between the power source and the electrodes, for generating a first phase of the biphasic countershock having a first polarity across the electrodes;

inverter means, separate from the capacitance means and electrically connected between the power source and the electrodes, for generating a second phase of the biphasic countershock having a second and opposite polarity across the electrodes and actively drawing low voltage electrical energy directly from the power source during delivery of the second phase; and control means, operatively coupled to the power source, the capacitance means and the inverter means, for controlling delivery of the first phase of the biphasic countershock from the capacitance means and the second phase of the biphasic countershock from the inverter means in response to a sensing of a cardiac dysrhythmia.

2. The apparatus of claim 1 in which the inverter means comprises an oscillator circuit.

3. The apparatus of claim 2 in which the oscillator circuit comprises a transformer having a primary winding electrically connected in series with a switch and the power source and a secondary winding electrically connected in series with a rectifier and a switch between the electrodes.

4. The apparatus of claim 1 in which the inverter means comprises:

an inductor, having a first end electrically connected in series with a rectifier and a switch to a first electrode and having the power source connected to the first end, and a second end connected to a second electrode; and a zener diode having a first end connected between the rectifier and the switch and a second end connected to the second electrode.

5. The apparatus of claim 4 in which the inverter means further comprises a capacitor connected in parallel with the zener diode, the capacitor having a first end connected at the first end of the zener diode and a second end connected to the second end of the zener diode.

6. The apparatus of claim 1 wherein the inverter means comprises a charge pump circuit.

7. The apparatus of claim 1 wherein the internal power source comprises:

a low voltage power source; and means for selectively charging the capacitance means to a high voltage from the low voltage power source.

8. The apparatus of claim 1 wherein the low voltage power source has a voltage output of less than 20 volts and the high voltage is at least 500 volts.

9. The apparatus of claim 1 wherein the low voltage electrical energy of the second phase of the biphasic countershock has a low voltage of less than 50 volts.

10. The apparatus of claim 8 wherein the low voltage of the second phase is in a voltage range of between 15 and 40 volts.

11. A method for operating an implantable cardioverter defibrillator device implanted within a human patient and electrically connected to at least two implantable electrodes located proximate a human heart to treat a cardiac arrhythmia by delivering an active biphasic electrical countershock having a high voltage first phase and a low voltage second phase, the method comprising the device-implemented steps of:

(a) sensing for a cardiac arrhythmia in a human patient;

(b) in response to a sensing of a cardiac arrhythmia, performing the steps of:

(b1) charging a capacitive charge storage system to a high voltage charge value using a low voltage power source;

(b2) discharging at least a portion of the charge value stored in the capacitive charge storage system through the electrodes to produce the high voltage first phase of the biphasic countershock;

(b3) generating the low voltage second phase of the biphasic countershock by using an active supply of low voltage electrical energy from the low voltage power source that is discharged through the electrodes to produce the second phase of the biphasic countershock having an opposite polarity from the first phase.

12. The method of claim 11 wherein step (b3) is accomplished using an inverter circuit.

13. The method of claim 11 wherein step (b3) is accomplished using an oscillator circuit.

14. The method of claim 11 wherein step (b3) is accomplished using a charge pump circuit.

15. The method of claim 11 wherein the low voltage power source has a voltage output of less than 20 volts and the high voltage charge value is at least 500 volts.

16. The method of claim 11 wherein the second phase of the biphasic countershock has a low voltage of less than 50 volts.

17. The method of claim 16 wherein the low voltage of the second phase is in a voltage range of between 15 and 40 volts.

* * * * *